(12) United States Patent
Wu et al.

(10) Patent No.: US 7,008,621 B2
(45) Date of Patent: Mar. 7, 2006

(54) REGULATION OF APOPTOSIS IN AQUATIC ORGANISMS BY AQUABIRNAVIRUS

(75) Inventors: Jen-Leih Wu, Taipei (TW); Jiann-Ruey Hong, Taipei (TW)

(73) Assignee: Academia Sinica, Taipei (TW)

(*) Notice: Subject to any disclaimer, the term of this patent is extended or adjusted under 35 U.S.C. 154(b) by 0 days.

(21) Appl. No.: 10/393,268

(22) Filed: Mar. 21, 2003

(65) Prior Publication Data

US 2003/0180325 A1    Sep. 25, 2003

Related U.S. Application Data

(60) Division of application No. 10/080,656, filed on Feb. 25, 2002, now Pat. No. 6,630,456, which is a continuation-in-part of application No. 09/706,869, filed on Nov. 7, 2000, now abandoned.

(60) Provisional application No. 60/167,010, filed on Nov. 23, 1999.

(51) Int. Cl.
| | |
|---|---|
| A01N 55/00 | (2006.01) |
| C12N 7/00 | (2006.01) |
| C12N 9/00 | (2006.01) |
| A01K 61/00 | (2006.01) |

(52) U.S. Cl. ............... 424/93.1; 424/93.1; 435/235.1; 435/325; 119/210; 119/215

(58) Field of Classification Search ............... 424/93.1, 424/93.2; 435/235.1, 325; 119/210, 215
See application file for complete search history.

(56) References Cited

U.S. PATENT DOCUMENTS 6,953,786 B1 * 10/2005 Pandol et al. ............... 514/183

OTHER PUBLICATIONS

Hong et al. J. Virol. Jun. 1999, vol. 73, No. 6, pp. 5056-5063.*
Hong et al. Virus Research Sep. 1999, vol. 63, pp. 75-83.*
Nakagawa et al. (J. Cancer Res. Clin. Oncol. 2000, vol. 126, pp. 448-454.*
Frost et al. The Prostate 1999, vol. 41, pp. 20-30.*
Velazquez et al. J. Exp. Clin. Cancer Res. 1998, vol. 17, No. 3, pp. 277-284.*

* cited by examiner

*Primary Examiner*—James Housel
*Assistant Examiner*—BaoQun Li
(74) *Attorney, Agent, or Firm*—Fei-Fei Chao; Bingham McCutchen LLP

(57) ABSTRACT

The present invention provides a mechanism for studies of apoptosis in aquatic organisms by infecting the aquatic organisms with aquabirnavirus, especially infectious pancreatic necrosis virus (IPNV). The infection of IPNV in an aquatic cell such as a Chinook salmon embryo cell (CHSE-214) converts the cell into an apoptotic cell. The present invention also provides a method for monitoring the morphological changes during apoptosis by cloning EGFP (a variant type of GFP) to an aquatic cell and monitoring the fluorescence using microscopic techniques. The intensity of the fluorescence reflects the expression of EGFP in cells. Finally, the present invention provides means for inducing or preventing/rescuing apoptosis in a host, which include aquatic and vertebrate. The apoptosis can be induced by IPNV infection or VP3 transfection that VP3 is a 32 kDa protein derived from IPNV segment A. The apoptosis can be prevented or rescued by an antisense VP3 RNA or a zfMcl-1a protein.

4 Claims, 25 Drawing Sheets

Fig. 23 pEGFP-VP3 pEGFP-VP3
+ VP3
antisense RNA

REGULATION OF APOPTOSIS IN AQUATIC ORGANISMS BY AQUABIRNAVIRUS

RELATED INVENTION

This patent application is a divisional of U.S. patent application Ser. No. 10/080,656, filed on Feb. 25, 2002 now U.S. Pat. No. 6,630,456, which in turn is a CIP of U.S. patent application Ser. No. 09/706,869, filed on Nov. 7, 2000 (now abandoned), which in turn claims the priority of U.S. Provisional Application Ser. No. 60/167,010, filed on Nov. 23, 1999, which are incorporated herein by reference.

FIELD OF THE INVENTION

The present invention, certain aspects of which are published in *Virus Research* (1999), 63:75–83 and *J. Virol.* (1999), 73:5056–5063 (which are herein incorporated by reference), relates to apoptosis in aquatic organisms induced by aquabirnavirus, preferably infectious pancreatic necrosis virus (IPNV). It also relates to methods to regulate apoptosis in aquatic cells by controlling the expression of Mcl-1 gene and pre-treating the aquatic cells with drugs which block the viral replication. It further relates to a method for monitoring the progress of apoptosis using EGFP (a variant type of green fluorescent protein [GFP]) as a probe.

BACKGROUND OF THE INVENTION

Infectious pancreatic necrosis virus (IPNV) is an economically important fish pathogen. IPNV belongs to a group of viruses known as Birnaviridae (Brown (1986), *Intervirology*, 25:141–143). Other members of Birnaviridae include infectious bursal disease virus (IBDV) of fowl and *Drosophila* X virus. IPNV was discovered to be associated with a highly contagious disease of susceptible hatchery-reared trout and salmonoids. As the name indicates, the infection among trout produces marked pancreatic necrosis, but histopathological changes sometimes also occur in adjacent adipose tissue, in renal hematopoietic tissue, in the gut, and in the liver (Wolf et al. (1960), *Proc. Soc. Exp. Biol. Med.*, 104:105–108). Histopathological changes can also occur in renal excretory and hematopoietic tissues, as first reported by Yasutake et al. (1965), *Ann. N.Y. Acad. Sci.*, 126:520–530. Although renal damage is consistent with the high titer of virus typically found in kidneys, at least in carrier fish, focal degeneration of liver parenchymal cells in yearling Atlantic salmon which had been previously inoculated with IPNV was also noted (Swanson and Gillespie (1979), *J. Fish. Res. Board Can.*, 36:587–591).

IPNV shows a high degree of antigenic heterogeneity. Three different stereotypes, Ab, Sp and VR299 (MacDonald and Gower (1981), *Virology*, 114:187–195; Okamoto et al. (1983), *Eur. J. Fish Dis.*, 6:19–25) and ten subgroups (Heppell et al. (1992), *J. Gen. Virol.*, 73:2863–2870) have been identified. IPNV is the etiological agent of a contagious, high mortality disease of young, hatchery-reared salmonids (Wolf et al. (1960), supra) and other non-salmonid fishes (Adair and Ferguson (1981), *J. Fish Dis.*, 4:69–76). IPNV is a double-stranded RNA virus with four virion proteins (MacDonald and Dobos (1981), *Virology*, 114:414–422).

Birnaviruses possess a bisegmented (A and B), double-stranded RNA genome contained within a medium-sized, unenveloped, icosahedral capsid. Birnavirus gene expression involves the production of four unrelated major genes that undergo various post-translational cleavage to generate three to five structural proteins (Dobos, P. 1995. Annu. Rew. Fish Dis. 5, 25–54). The largest protein (90 kDa), VP1, is encoded by the smaller segment B genome, and the larger genome segment A encodes VP2 (42 kDa), VP4 (28 kDa) and VP3 (32 kDa). Genome segment A contains an additional small open reading frame (ORF) which overlaps the amino terminal end of the polyprotein from the reading frame (Duncan, R., Nagy, E., Krell, P. J. and Dobos, P. 1987. J. Virol. 61, 3655–3664). This small ORF encodes a 17 kDa arginine-rich minor polypeptide, VP5, which is produced in small quantities and is synthesized during the early replication cycle (Magyar, G. & Dobos, P. 1994. Virology 204, 580–589).

There are two major morphologically and biochemically distinct modes of death in eukaryotic cells: apoptosis and necrosis (Duvall and Wyllie (1986), *Immunol. Today*, 7:115–119). Apoptosis is a physiological process involved in normal tissue turnover that occurs during embryogenesis, aging, and tumor regression, but pathological stimuli, such as viral infections (Gougeon and Montagnier (1993), *Science*, 260:1269–1270), can also be triggering factors. Typically, apoptotic cell death is characterized by nuclear condensation, endonucleolytic degradation of DNA at nucleosomal intervals ("laddering"), and plasma membrane blebbing (Wyllie et al. (1980), *Int. Rev. Cytol.*, 68:251–306). Necrosis is a pathological reaction that occurs in response to perturbations in the cellular environment such as complement attack, severe hypoxia, or hyperthermia. These stimuli increase the permeability of the plasma membrane, resulting in irreversible swelling of the cells (Wyllie et al,(1980), supra).

Apoptosis is important during embryonic development, metamorphosis, tissue renewal, hormone-induced tissue atrophy and many pathological conditions. In multi-cellular organisms, apoptosis ensures the elimination of superfluous cells including those that are generated in excess, have already completed their specific functions or are harmful to the whole organism. In reproductive tissues, massive cell death occurs under the control of hormonal signals. A growing body of evidence suggests that the intracellular "death program" activated during apoptosis is similar in different cell types and conserved during evolution. (Hengartner and Horvitz (1994), *Cell*, 76:1107–1114). In addition to being essential for normal development and maintenance, apoptosis is important in the defense against viral infection and in preventing the emergence of cancer.

Apoptosis involves two essential steps. The "decision" step is controlled by the Bcl-2 family of proteins which consists of different anti- and pro-apoptotic members. The "execution" phase of apoptosis is mediated by the activation of caspases and cysteine proteases that induce cell death via the proteolytic cleavage of substrates vital for cellular homeostasis.

Bcl-2 protein is a 25 kD integral membrane protein of the mitochondria. Bcl-2 protein extends survival in many different cell types by inhibiting apoptosis elicited by a variety of death-inducing stimuli (Korsmeyer (1992), *Blood*, 80:879–886). Overexpression of bcl-2 has been related to hyperplasia, autoimmunity and resistance to apoptosis (Fang et al. (1994), *J. Immunol.*, 153:4388–4398). Bcl-2 contains a family of related genes, which includes, but is not limited to, A1, mcl-1, bcl-w, bax, bad, bak and bcl-x. A1, mcl-1, bcl-2 and bcl-x1 (long form of bcl-x) are presently known to confer protection against apoptosis and are referred to herein as "anti-apoptotic bcl-2 related proteins". In contrast, bax, bad, bak and bcl-xs (short form of bcl-x) are presently known to promote cell death by inhibiting this protective effect.

Mcl-1 is one of the members of the Bcl-2 family. Like Bcl-2, Mcl-1 heterodimerizes with Bax, an accelerator of apoptosis in the Bcl-2 family, and neutralizes the cytotoxicity induced by Bax in yeast (Bodrug et al. (1996), *Death Differ.*, 2:173–182). Mcl-1 is also able to protect Chinese hamster ovary cells from apoptosis induced by c-myc overexpression (Reynolds et al. (1994), *Cancer Res.*, 54:6348–6352). This protein was discovered as a novel gene induced early in the induction of differentiation of a human myeloid leukemia cell line (Kozopas et al. (1993), *Proc. Natl. Acad. Sci.* USA, 90:3516–3520). Expression of Mcl-1 mRNA was rapidly up-regulated with phorbol ester in those cells followed by a rapid degradation, consistent with the presence of a mRNA destabilization sequence in its 3'-untranslated region. The half-life of the Mcl-1 protein is short (Yang et al. (1995), *J. Cell Biol.*, 128:1173–1184), which has been ascribed to the presence of two PEST (proline, glutamic acid, serine, threonine) motifs. Therefore, Mcl-1 is suggested as a rapidly inducible, short-term effector of cell viability (Yang et al. (1996), *J. Cell. Physiol.*, 166:523–536). Recently, Hong et al. (*Virology,* (1998), 250:76–84) reported that an E1-S of IPNV Ab strain induced apoptosis in CHSE-214 cells. Hong et al.'s publication is herein incorporated by reference. In Hong et al.'s report, four kinds of detecting methods were used to determine whether apoptosis is involved in fish embryonic cell death after IPNV infection: (1) assay with terminal deoxynucleotidyl transferase (TdT)-mediated end-labeling of DNA in nuclei of intact cells during virus infection; (2) assay for procoagulant activity; (3) assay for DNA ladders; and (4) electron microscopic assays for the ultrastructural changes in characteristic apoptotic cells.

The results show that apoptosis precedes any detectable necrotic change in CHSE-214 cells, suggesting that apoptosis characterizes the onset of pathology in host cells and is followed by necrotic processes. Hong et al.'s report is important because previously, IPNV infection is only viewed as caused by a necrotic process. However, Hong et al.'s report did not provide any insights which delineate the apoptotic process from necrosis.

In the present invention, an investigation of apoptosis is carried out by using CHSE-214 cells infected with IPNV as a model. The investigation is conducted by transfecting the cells with a pEGFP vector which enables the cells to express EGFP (a variant type of GFP [green fluorescent protein]). Based on the special characteristics of EGFP which can fluorescence 35 times more intense than the wild-type GFP, the morphological changes during apoptosis are monitored, which show that IPNV causes CHSE-214-EGFP cells to undergo apoptosis, then a nontypical apoptosis, and finally, postapoptotic necrosis in cells. The discovery of the nontypical apoptosis stage before necrosis takes place is one of the novel findings in the present invention.

The present invention also provides studies of apoptosis via an Mcl-1 dependent pathway. The results of the present invention indicate that the occurrence of apoptosis is due to down regulation of the Mcl-1 gene caused by viral infection. In addition, various drugs or chemicals are tested for their capacity of preventing the down-regulation of Mcl-1 protein expression by viral infection. The results show that by blocking the down regulation of the Mcl-1 gene, the cell death caused by IPNV infection is effectively prevented.

The present invention is important because it not only provides a model for studies of apoptosis but also provides a means for preventing or containing widespread of IPNV infection in aquatic organisms.

SUMMARY OF THE INVENTION

The present invention provides an aquatic apoptotic cell which can be used as a model for studying morphological changes during apoptosis. The aquatic apoptotic cell is induced by infecting an aquatic cell with an aquabimavirus. The preferred aquatic cell is a fish cell. The preferred fish cell includes, but is not limited to, salmon, trout, grouper, and eel cells. The most preferred fish cell is Chinook salmon embryo cell (CHSE-214). The preferred aquabimavirus is an infectious pancreatic necrosis virus (IPNV). The preferred IPNV is E1-S of IPNV Ab strain which is isolated from Japanese eel in Taiwan (Wu et al. (1987), *Bull. Inst. Zool. Acad. Sinica,* 26:201–214). The infectious period is preferred not to exceed 8 hours.

The morphological changes of the aquatic apoptotic cell during apoptosis can be monitored by fluorescence using EGFP as a probe. EGFP is introduced into the aquatic cell by transfecting the cell with a pEGFP-N1 vector. By using EGFP, a nontypical apoptotic process is discovered which occurs after a typical apoptosis and before the necrosis process. This nontypical apoptosis features, including highly condensed membrane blebbing, occurs during the middle apoptotic stage. At the pre-late apoptotic stage, membrane vesicles quickly formed, blebbed, and are finally pinched off from the cell membrane. Together, these findings show the apoptotic features at the onset of pathology in host cells (early and middle apoptotic stages), followed secondarily by nontypical apoptosis (pre-late apoptotic stage) and then by postapoptotic necrosis (late apoptotic stage), of a fish cell. The results also demonstrate that nontypical apoptosis is a component of IPNV-induced fish cell death.

The present invention also provides agents for inducing or preventing/rescuing apoptosis. The first agent for inducing apoptosis is IPNV itself. The second agent for inducing apoptosis is VP3, a 32-kDa protein derived from the IPNV segment A. The nucleotide sequence of VP3 is publicly available, as accession number AF291752 in National Center for Biotechnology Information (NCBI) gene data bank. The VP3 gene can be converted into cDNA by RT-PCT and inserted into a plasmid to transfect a host organism or a cell line.

The first agent for preventing/rescuing apoptosis caused by IPNV or VP3 is an antisense RNA of VP3, which can be transfected into a host or a cell line. The second agent for preventing/rescuing apoptosis caused by IPNV or VP3 is a zfMcl-1a gene, which can be inserted into a plasmid (such as pEGFP-zfMcl-1a) for transfection into a host or a cell line.

The present invention also includes two methods for detecting apoptosis. The first method provides a means to visualize morphological changes during apoptosis. The method contains the following steps: (1) transfecting the aquatic cells with a pEGFP-N1 vector; (2) infecting the aquatic cell with an aquabimavirus; and (3) monitoring the morphological changes by a microscopic technique. The pEGFP-N1 vector is driven by an immediate-early promoter of human cytomegalovirus. The coding region contains the EGFP gene, which contains a chromophore mutation which produces fluorescence 35 times more intense than that of wide-type GFP (green fluorescence protein). GFP is a revolutionary molecule which can be used to monitor gene expression and fusion protein localization in vivo or in situ and in real time. GFP is from the jellyfish *Aequorea victoria*.

The transfected cells can be screened by G418. The preferred aquabirnavirus is IPNV. The preferred aquatic cell is CHSE-214. The microscopic technique includes, but is not limited to, light microscopy, fluorescence microscopy, scanning electron microscopy, and immuno-electron microscopy.

The second method provides quantitative measurements of apoptosis. The method contains the following steps: (1) transfecting an aquatic cell with a pEGFP-N1 vector; (2) infecting the aquatic cell with an aquabimavirus; and (3) measuing EGFP in the aquatic cell and in the culture medium. EGFP is measured based upon the fluorescence intensity. The pEGFP-N1 transfected aquatic cell produces EGFP which can be evaluated by a Fluorolite 1000 (DYNEX)

Furthermore, the present invention provides methods for inducing or preventing apoptosis in vivo or in vitro. The first method for inducing apoptosis includes in vivo infection of aquatic organisms with an aquabimavirus. The preferred aquabimavirus is IPNV. The preferred IPNV is E1-S of IPNV Ab strain which is isolated from Japanese eel in Taiwan (Wu et al. (1987), supra). The preferred aquatic organisms are embryos or hatchery-reared juvenile salmonids and nonsalmonid fish. Salmonid fish include, but are limited to, pacific salmon in general (*Oncorhynchus* sp.), such as rainbow trout (*Oncorhynchus mykiss*), brook trout (*Salvelinus fontinolis*), chinook salmon (*Oncorhynchus tshawytscha*), coho salmon (*Oncorhynchus kisutch*), sockeye salmon (*Oncorhynchus nerca*) and Atlantic salmon (*Salmo salar*). Nonsalmonid fish includes carp, perch, pike, eels and char. Certain mollusks and crustaceans can also be infected with IPNV.

This method also applies to in vitro transfection of IPNV into fish cell lines, such as CHSE-214 (an embryo cell line from salmon). The preferred temperature for infected cultures is at 18° C. The induction of apoptosis by aquabirnavirus can be prevented by pretreatment of cyclohexamide (protein synthesis inhibitor), genistein (tyrosine kinase inhibitor), and EDTA (cation chelator) prior to viral infection.

The second method for inducing apoptosis includes transfection of a VP3 gene-containing plasmid into a host, which may be an aquatic/vetebrate organism or cell line, to overexpress VP3 in the host. VP3 is a 32-kDa protein derived from the IPNV segment. The nucleotide sequence of VP3 is publicly available, as accession number AF 291752 in NCBI gene data bank.

The VP3 gene of IPNV can be converted into DNA by RT-PCR and constructed into a plasmid containing EGFP to form a pEGFP-VP3 by techniques which are known to persons with ordinary skill in the art. The preferred aquatic host includes salmonids and nonsalmonid fish. Salmonid fish include, but are limited to, pacific salmon in general (*Oncorhynchus* sp.), such as rainbow trout (*Oncorhynchus mykiss*), brook trout (*Salvelinus fontinolis*), chinook salmon (*Oncorhynchus tshawytscha*), coho salmon (*Oncorhynchus kisutch*), sockeye salmon (*Oncorhynchus nerca*) and Atlantic salmon (*Salmo salar*). Nonsalmonid fish includes carp, perch, pike, eels, zebrafish and char. The preferred vetebrate host includes rat, hamster and human. The preferred aquatic or vertebrate organism is embryo. The pEGFP-VP3 can transfect with liposome to cell lines or a vertebrate embryo by microinjection by commonly known methods. The preferred cell lines for induction of apoptosis by VP3 include CHSE-214 (an embryo cell line from salmon), NIH3T3 (mice fibroblast), CHO (Chinese hamster ovary cell), and Hepa 3b and Hepa G2 cells (human liver tumor cells).

The third method for inducing apoptosis include down regulating Mcl-1 gene expression. The down regulation of Mcl-1 gene expression correlates to IPNV replication. The preferred aquatic organisms are fish, in particular fish cells derived from salmon, trout, grouper, and eel. The down regulation of Mcl-1 gene expression can be blocked by drugs such as cyclohexamide (protein synthesis inhibitor), genistein (tyrosine kinase inhibitor), and EDTA (cation chelator). These drugs help to maintain Mcl-1 expression level and block the induction of DNA internucleosomal cleavage (i.e., blocking the intense DNA laddering pattern), so as to rescue or delay the apoptotic cell death process.

The first method for preventing or rescuing apoptosis by IPNV infection or VP3 transfection requires transfecting an antisense RNA of VP3 into a host, which may be an aquatic/vertebrate organism or cell line. The preferred aquatic host includes salmonids and nonsalmonid fish. Salmonid fish include, but are limited to, pacific salmon in general (*Oncorhynchus* sp.), such as rainbow trout (*Oncorhynchus mykiss*), brook trout (*Salvelinus fontinolis*), chinook salmon (*Oncorhynchus tshawytscha*), coho salmon (*Oncorhynchus kisutch*), sockeye salmon (*Oncorhynchus nerca*) and Atlantic salmon (*Salmo salar*). Nonsalmonid fish includes carp, perch, pike, eels, zebrafish and char. The preferred vetebrate host includes rat, hamster and human. The preferred aquatic or vertebrate organism is embryo. The pEGFP-VP3 can transfect an aquatic or a vertebrate embryo by microinjection by commonly known methods. The preferred cell lines include CHSE-214 (an embryo cell line from salmon), NIH3T3 (rat fibroblast), CHO (hamster embryoic cells), and Hepa 3b and Hepa G2 cells (human liver tumor cells).

The second method for preventing or rescuing apoptosis from IPNV infection requires transfecting a zfMcl-1a into a host, which may be an aquatic/vertebrate organism or cell line. The nucleotide sequence of zfMcl-1a is publicly available, which is ZfMcl-1a accession number AF 231016 as published in NCBI gene data bank. The zfMcl-1a can be transfected into the host by microinjecting a zfMcl-1a-containing plasmid such as pEGFP-zfMcl-1a or pEGFP-C1. The preferred aquatic host includes salmonids and nonsalmonid fish. Salmonid fish include, but are limited to, pacific salmon in general (*Oncorhynchus* sp.), such as rainbow trout (*Oncorhynchus mykiss*), brook trout (*Salvelinus fontinolis*), chinook salmon (*Oncorhynchus tshawytscha*), coho salmon (*Oncorhynchus kisutch*), sockeye salmon (*Oncorhynchus nerca*) and Atlantic salmon (*Salmo salar*). Nonsalmonid fish includes carp, perch, pike, eels, zebrafish and char. The preferred vertebrate host includes rat, hamster and human. The preferred aquatic or vertebrate organism is embryo. The pEGFP-VP3 can transfected an aquatic or a vertebrate embryo by microinjection by commonly known methods. The preferred cell lines for preventing or rescuing apoptosis include CHSE-214 (an embryo cell line from salmon), NIH3T3 (mice fibroblast), CHO (Chinese hamster ovary cell), and Hepa 3b and Hepa G2 cells (human liver tumor cells).

BRIEF DESCRIPTION OF THE FIGURES

FIG. 1 shows the dynamics of the sequential morphological changes visualized by EGFP in living cells infected with IPNV. Monolayer cultures of CHSE-214 cells were transfected with pEGFP-N1 using Lipofectin and selected with G418. Cells were infected with virus (MOI of 1), and virus-infected cells were sequentially observed by fluorescence microscopy from 0 to 7 h post infection (p.i.) Scale bar, 3 μm. The arrows indicate the formation of membrane vesicles (MV) from the apoptotic cell.

FIG. 2 shows the analysis of DNA fragments in CHSE-214-EGFP cells after being infected with IPNV EI-S (MOI of 1). DNA was isolated from uninfected CHSE-214 cells as a negative control after 0 h (lane 2) and 8 h (lane 3) of incubation and from cells infected for 8 h with an MOI of 1 of E1-S (lane 4), electrophoresed through 1.2% agarose gels, and visualized by ethidium bromide staining. Lane 1 contained molecular size markers (1-kb DNA ladder).

FIG. 3 shows the scanning electron micrographs of CHSE-214 cells. (A) Negative control CHSE-214 cell. (B) Pre-late apoptotic CHSE-214 cell. The formation of membrane vesicles (MV) from the apoptotic cell is indicated by arrows. (C) Middle-late apoptotic cell. The formation of small holes is indicated by arrows. (D) Late apoptotic cell. Small holes left on the surfaces of apoptotic bodies from the IPNV-treated group are indicated by arrows. Scale bar, 1.5 μm.

FIG. 4 shows the patterns of EGFP release by CHSE-214-EGFP cells infected with IPNV. (A) shows the EGFP release patterns after IPNV infection by Western blotting. CHSE-214-EGFP cells were infected with IPNV (MOI of 1). Samples were electrophoresed on an SDS-polyacrylamide gel and electroblotted to a nitrocellulose membrane. The membrane either contained a rabbit polyclonal antiserum directed against EGFP (part a and c) or was stripped and reprobed with a mouse IgG monoclonal antibody directed against actin (part b). The chemiluminescent signal was imaged on Kodak XAR-5 film using a 3-min (part a), 1.5-min (part b), or 30-min (part c) exposure. (a) Lanes: 1: 0.45 μg of wild-type GFP; 2 to 7: 30 μg of virus-infected CHSE-214 cell lysate at 0, 2, 4, 6, 8, and 16 h postinfection (p.i.), respectively. (b) The nitrocellulose membrane in part a was stripped and reprobed with anti-actin monoclonal IgG. (c) A 30-μg sample of supernatant protein of IPNV-infected CHSE-214-EGFP cells at 0, 2, 4, 6, 8, 10, 12, and 24 h p.i., respectively. (B) shows the rate of EGFP release by CHSE-214-EGFP cells infected with IPNV. Cellular and culture medium EGFP samples were prepared for assay in EGFP release experiments. About $10^5$ cells per ml were seeded on a 60-mm petri dish and incubated for more than 20 h. Cells that received virus at an MOI of 1 were incubated for 0, 2, 4, 6, 8, 10, 12, and 24 h p.i. At the end of each incubation time, the IPNV-infected CHSE-214 cells and culture medium were collected to determine the concentration of retained EGFP. Both 5 μg of lysed virus-infected cells per sample and 30 μg of supernatant medium per sample were counted by a Fluorolite 1000. The EGFP concentrations of the lysed cells and supernatant were evaluated by using a Fluorolite 1000 to compare them with standard GFP protein and dividing by 35.

FIG. 5 shows the immunoelectron micrographs of ultrathin sections of CHSE-214-EGFP cells that were uninfected or infected with IPNV and labeled with anti-GFP IgG. (A) Normal CHSE-214-EGFP cell used as a negative (N) control on which labeled EGFP is present (arrows) and EGFP formed dimers. (B) CHSE-214-EGFP cell infected with IPNV (MOI of 1) at 8 h p.i. upon which labeled EGFP is present (small arrows). Nontypical apoptotic morphological changes were observed at this pre-late apoptotic cell stage such as the formation of membrane vesicles (MV) (large, long arrow) and, finally, the MV pinching off from the plasma membrane of the apoptotic cell (large, short arrow).

FIG. 6 is a western blot assay which shows the effect of chemical inhibitors on EGFP release. Protein synthesis inhibitors, serine proteinase inhibitors, tyrosine kinase inhibitors, and a cation chelator were added to CHSE-214-EGFP cells before infection with IPNV (MOI of 1). After infection, the cells were incubated for 16 h. Samples were electrophoresed on a 12% SDS-polyacrylamide gel and electroblotted to a nitrocellulose membrane. Antigen-specific signals were detected with either rabbit anti-GFP serum (A and C) or a mouse IgG monoclonal antibody directed against actin (B). The chemiluminescent signal was imaged on Kodak XAR-5 film by using a 5-min (A), a 1-min (B), or a 30-min (C) exposure. (A) Lanes: 1, 0.2 μg of recombinant wild-type GFP as a positive control; 2, normal CHSE-214-EGFP cell lysate; 3, 30 μg of cell lysate protein corresponding to IPNV infection; 4–9, 30 μg of cell lysate protein corresponding to pre-treatment with cycloheximide (CHX) (100 μg/ml), aprotinin (400 μg/ml), leupeptin (400 μg/ml), genistein (100 μg/ml), tyrphostin (100 μg/ml), and EDTA (2 mM) and then followed by virus infection for 16 h, respectively. (B) The nitrocellulose membrane from panel A was stripped and reprobed with an actin antibody. (C) Lanes: 1, 100 ng of wide-type GFP; 2, 30 μg of supernatant medium protein from normal CHSE-214 cells; 3, 30 μg of supernatant medium protein from IPNV-infected cells at 16 h p.i. 4–9, 30 μg of supernatant medium protein corresponding to treatment with cycloheximide (CHX) (100 μg/ml), aprotinin (400 μg/ml), leupeptin (400 μg/ml), genistein (100 μg/ml), tyrphostin (100 μg/ml), and EDTA (2 mM) and then followed by virus infection for 16 h, respectively.

FIG. 7 illustrates the morphological changes induced in fish cells by IPNV infection. (A) Normal attached cell. In the early stage of apoptosis, the cell detaches from the extracellular matrix (A to B, 0 to 3 h p.i.). In the middle stage, the apoptotic cell is rounded up (A to B, 3 to 6 h p.i.). To enter this pre-late apoptotic stage (B to C, 6 to 7 h p.i.), there is a rapid process which follows that includes MV formation and MV pinching off from the plasma membrane. In the middle stage, the apoptotic cell is left with small holes in the cell membrane (C to D, 7 to 8 h p.i.). Finally, in the late apoptotic stage, either membrane-bound apoptotic bodies (D to E, 8 to 12 h p.i.) are formed or a postapoptotic necrosis process occurs (D to F, 8 to 12 h p.i.) in which the condensed chromatin encloses the nuclear membrane.

FIG. 8 shows the scanning electron micrographs of CHSE-214 cells. (A) Uninfected CHSE-214 cells. (B) IPNV-infected CHSE-214 cells, showing membrane blebbing in the cell which is a typical indication of apoptosis.

FIG. 9 is an analysis of DNA fragments of IPNV E1-S-infected CHSE-214 cells by 1.2% agarose gel electrophoresis. Lane 1 contains the molecular weight markers used in the gel (1-kb DNA ladder from MBI Fermentas Inc. USA, for sizing liner fragments ranging in size from 500 bp to 1 kb). Lane 2 is a negative control using DNA isolated from uninfected CHSE-214 cells for 0 hour incubation. Lanes 3–5 represent DNA isolated from CHSE-214 cells after being infected by IPNV for 4, 8 and 12 hours with a MOI (multiplicity of infection) of 1. The agarose gel was stained with ethidium bromide.

FIG. 10 shows the detection of major proteins of IPNV E1-S strain on Western blots. Samples were electrophoresed on a SDS-polyacrylamide gel and electroblotted to a nitrocellulose membrane. Antigen-specific signals were detected with a rabbit anti-E1-S virion antiserum and a goat anti-rabbit IgG conjugated to alkaline phosphatase. The chemiluminescent signal was imaged on Kodak X-OMAT film (Eastman Kodak) with a 1.5-min exposure. Lanes 1–7 correspond to a MOI of 1 infected cells for 0, 2, 4, 6, 8, 10 and 24 h post-infection.

FIG. 11 shows the detection of Mcl-1 protein in CHSE-214 by IPNV infection on Western blots. CHSE-214 cells were infected with IPNV (MOI of 1). Samples were electrophoresed on a SDS-polyacryamide gel and electroblotted to a nitrocellulose membrane. The nitrocellulose membrane was stained with either a rabbit polyclonal antiserum directed against human MCL-1 (Pharmingen) or mouse monoclonal IgG antibodies directed against actin (Amershan) (B). The chemiluminescent signal was imaged on Kodak XAR-5 film using a 3-min (A) and 1.5-min (B) exposure. (A) Lanes 1–7, 30 μg of virus infected CHSE-214 cell lysate corresponding to 0, 2, 4, 6, 8, and 24 h postinfection, respectively. (B) The nitrocellulose membrane of (A) was stripped in stripping buffer containing 62.5 mM Tris-HCl (pH 6.8), 3.0% (w/v) SDS, and 50 mM 1,4-dithiothreitol for 30 min at 55° C. with gentle shaking to remove the primary (Mcl-1) and secondary antibodies (peroxidase-labeled goat anti-rabbit conjugate). The blots were then washed four times for 10 min each time in PBS containing 0.1% (v/v) Tween 20 and reprobed with mouse actin monoclonal antibody (1/1500, Chemicon) and a 1:7500 dilution of a peroxidase-labeled goat anti-mouse conjugate (Amersham).

FIG. 12 shows the effect of blocking viral protein expression by drugs on Western blots. After adding protein synthesis inhibitor, serine proteinase inhibitors, tyrosine kinase inhibitors and a cation chelator, CHSE-214-EGFP cells were infected with IPNV (MOI of 1) then incubated for 16 h at 18° C. Samples were electrophoresed on a 12% SDS-polyacrylamide gel and electroblotted to a nitrocellulose membrane. Antigen-specific signals were detected with a rabbit anti-EI-S virion antiserum (A) or with a rabbit anti-human Mcl-1 antiserum (Pharmingen) (B) and with a mouse monoclonal IgG antibody directed against mouse actin (Chemicon) (C). (A) Lane 1, normal CHSE-214 cell lysate; lane 2, IPNV infected cell lysate at 16 h postinfection; lanes 3–8, 30 μg of cell lysate, to which was added cycloheximide (100 μg/ml), aprotinin (400 μg/ml), leupeptin (400 μg/ml), genistein (100 μg/ml), tyrphostin (100 μg/ml) and EDTA (2 mM), followed by IPNV infection and incubated cells for 16 h, respectively. (B,C) The nitrocellulose membrane from (A) was stripped and reprobed with Mcl-1 or an actin antibody, respectively.

FIG. 13 shows the effect of certain drugs on preventing host cell DNA internucleosomal cleavage prior to IPNV E1-S (MOI of 1) infection. Lane 2: DNA isolated from uninfected CHSE-214 cells as a negative control. Lane 3: cells infected for 16 h with an MOI of 1 of E1-S, respectively, at 16 h postinfection. Lanes 6 and 7: CHSE-214 cells treated with aprotinin (400 μg/ml) in the absence and presence of infection by an MOI of 1 of E1-S, respectively, at 16 h postinfection. Lanes 8 and 9: CHSE-214 cells treated with leupeptin (400 μg/ml) in the absence and presence of infection by an MOI of 1 of E1-S, respectively, at 16 h postinfection. Lanes 10 and 11: CHSE-214 cells treated with genistein (100 μg/ml) in the absence and presence of infection by an MOI of 1 of E1-S, respectively; at 16 h postinfection. Lanes 12 and 13: CHSE-214 cells treated with tyrphostin (100 μg/ml) in the absence and presence of infection by an MOI of 1 of E1-S, respectively, at 16 h postinfection. Lanes 14 and 15: CHSE-214 cells treated with 2 mM EDTA in the absence and presence of infection by an MOI of 1 of E1-S, respectively, at 16 h postinfection. All samples were electrophoresed through 1.2% agarose gels and visualized by ethidium bromide staining. Lane 1 contains the molecular weight marekers used in the gel (1 kb DNA ladder from MBI for sizing linear fragments ranging in size from 500 bp to 1 kb).

Figure 16:
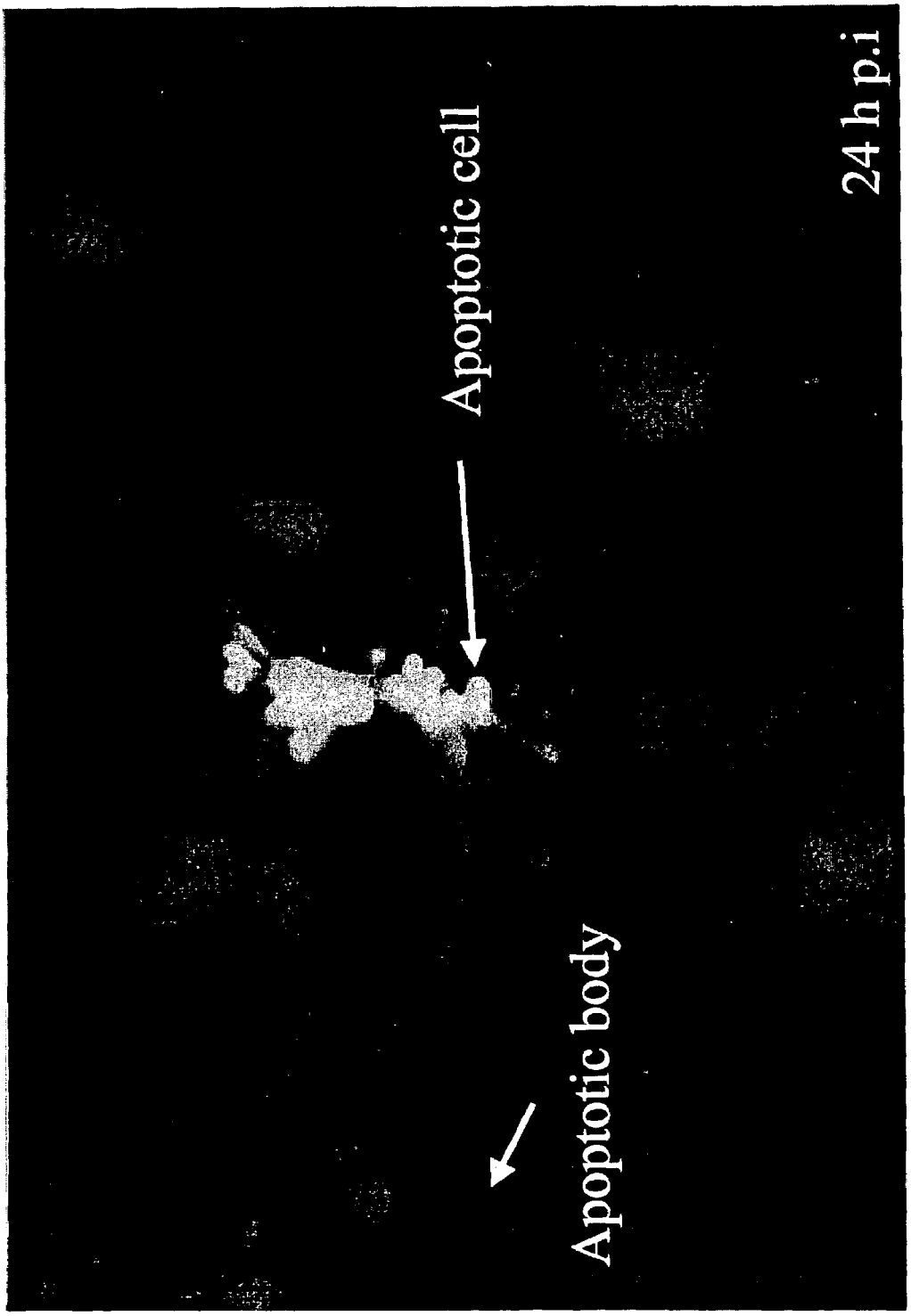

FIG. 16 shows the induction of apoptosis in NIH3T3 cells due to overexpression of IPNV VP3. A fused gene, EGFP-VP3 has been generated in plasmid. The EGFP-VP3 plasmid was then transfected to NTH3T3 cells in the together with lipofectamine. The micrograph shown in the figure was taken 24 hours after IPNV infection that apoptotic cell indicated by long arrow and apoptotic body indicated by short arrow.

Figure 17:
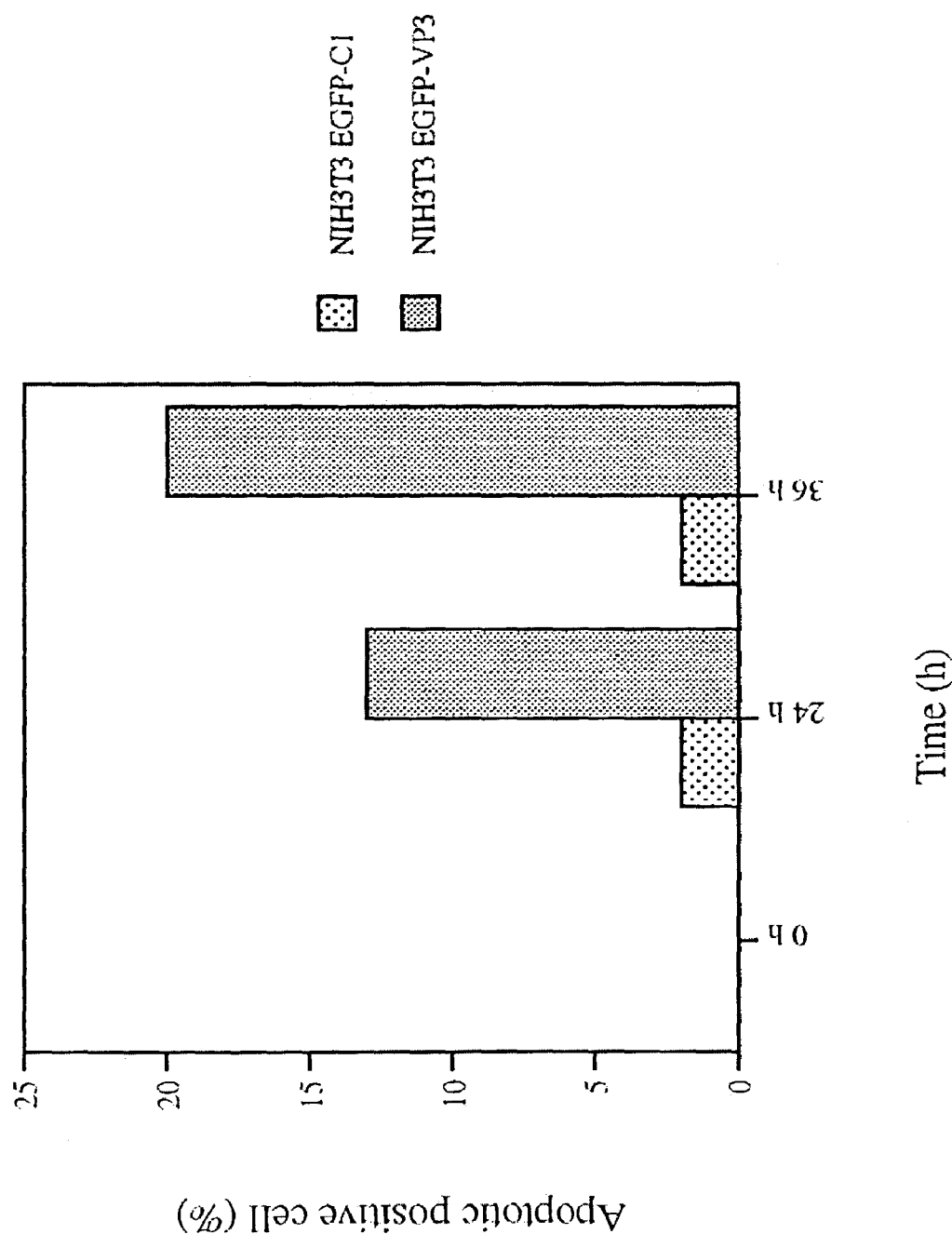

FIG. 17 shows % of apoptotic positive cells in NIH3T3 cell line 24 or 36 hours after being transfected with EGFP-C1 or EGFP-VP3: transfected with EGFP-C1 (all 2% at 24 or 36 h); transfected with EGFP-VP3 (13% at 24 h and 20.5% at 36 h).

Figure 18:
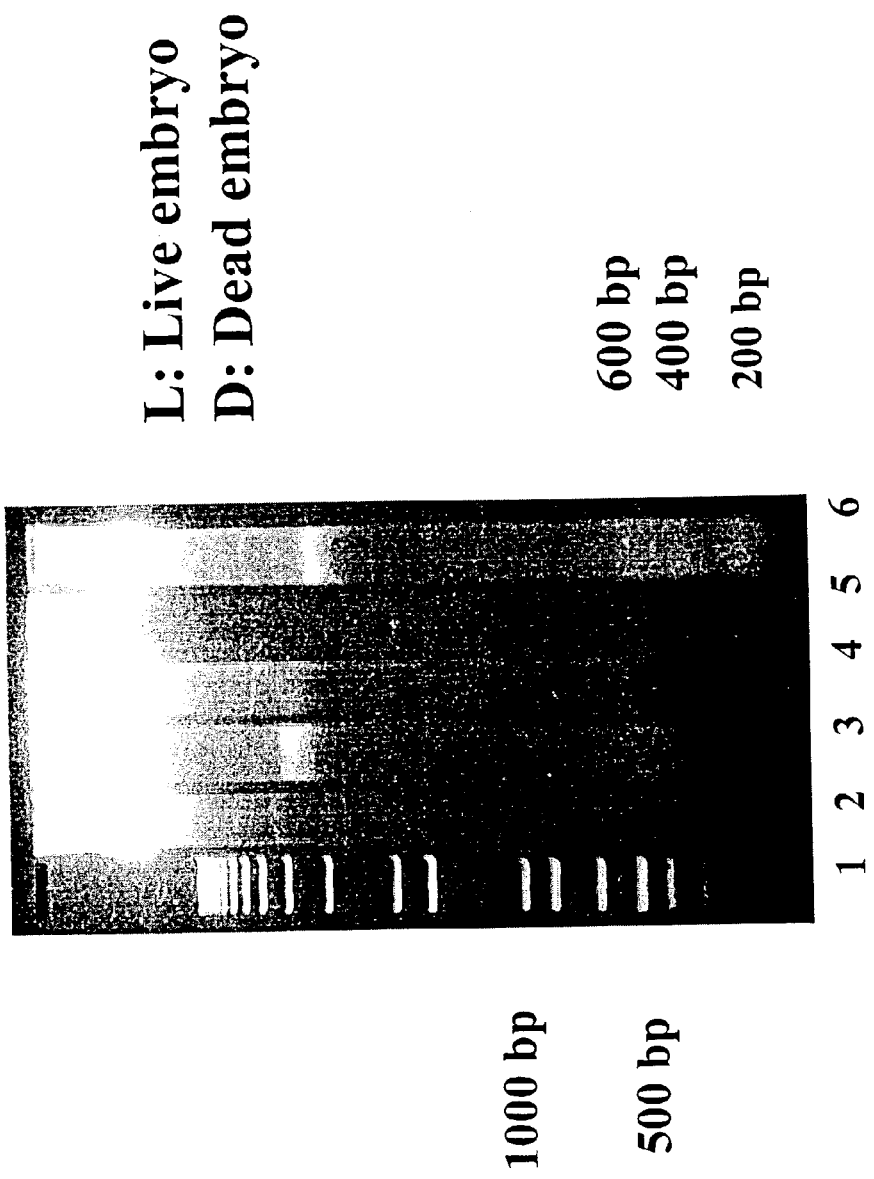

FIG. 18 shows induction of internucleosomal cleavage by VP3 in zebrafish embryonic cell. DNA fragments was examined in 1.2% agarose gel after microinjection of pEGFP-VP3 or pEGFP-C1 into zebrafish embryos. L: Live zebrafish embryo; D: Dead zebrafish embryo. Lane 1: DNA size marker; Lane 2: Live embryo after receiving pEGFP-C1 for 12 hours (control); Lane 3: Dead embryo after receiving pEGFP-C1 for 12 hours (control); Lane 4: Live embryo after receiving pEGFP-VP3 for 12 hours; Lane 5: Dead embryo after receiving pEGFP-VP3 for 4 hours; Lane 6: Dead embryo after receiving pEGFP-VP3 for 12 hours (which shows intense DNA fragmentation).

Figure 19:
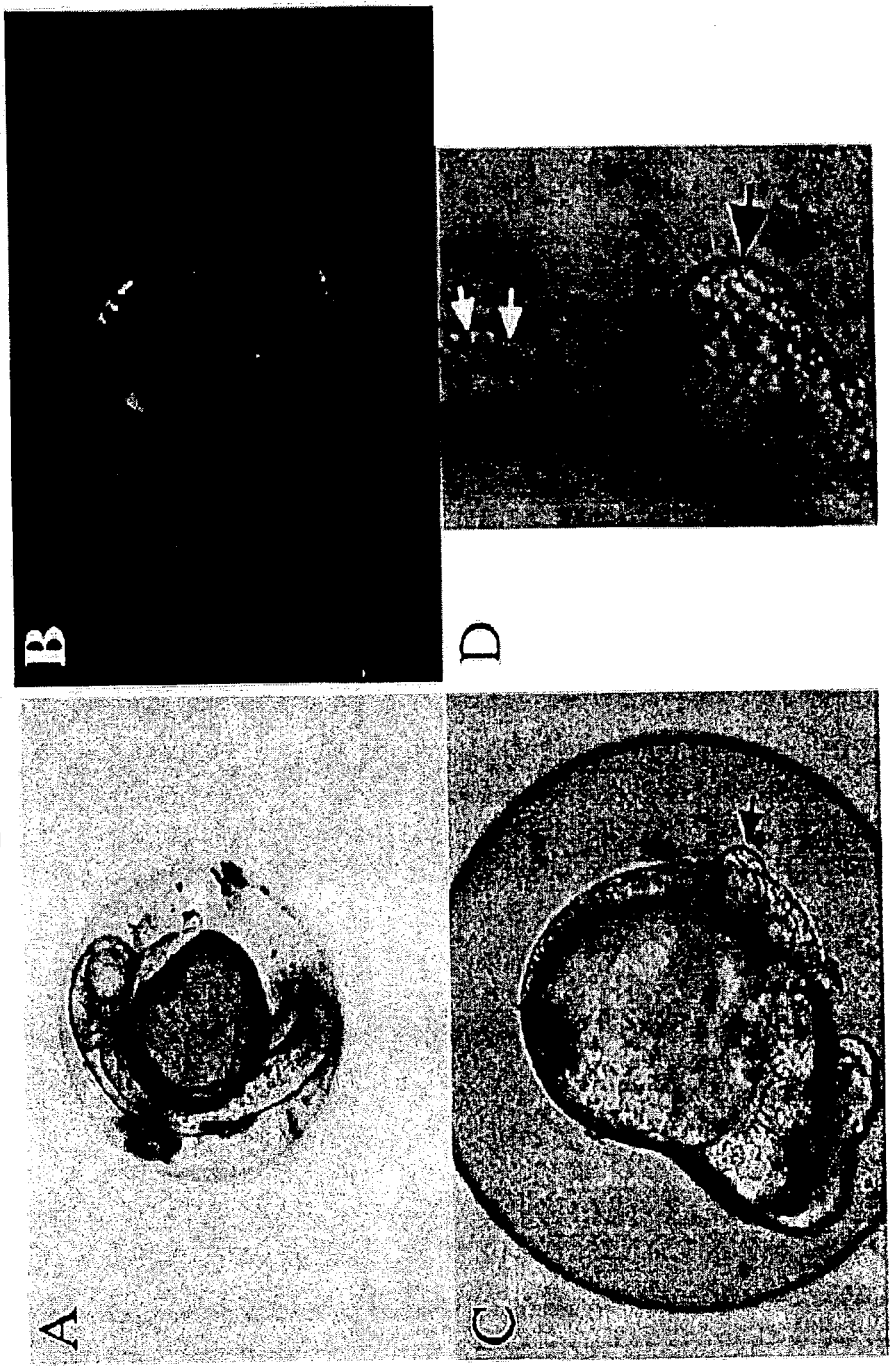

FIG. 19 shows VP3-induced apoptotic cell death in zebrafish embryos and damage in the somite after microinjection with pEGFP-VP3 for 24 hours. FIGS. 19A and B are zebrafish embryos after injected with pEGFP-C1 (negative controls), in which FIG. 19A was brightfield image (taken under light microscope) and FIG. 19B was fluorescence image (taken under fluorescence microscope); FIGS. 19C and D are injected with pEGFP-VP3. Shown in FIG. 19D are areas containing flattened dead cells (⇐) and damaged somite (◆).

Figure 20:
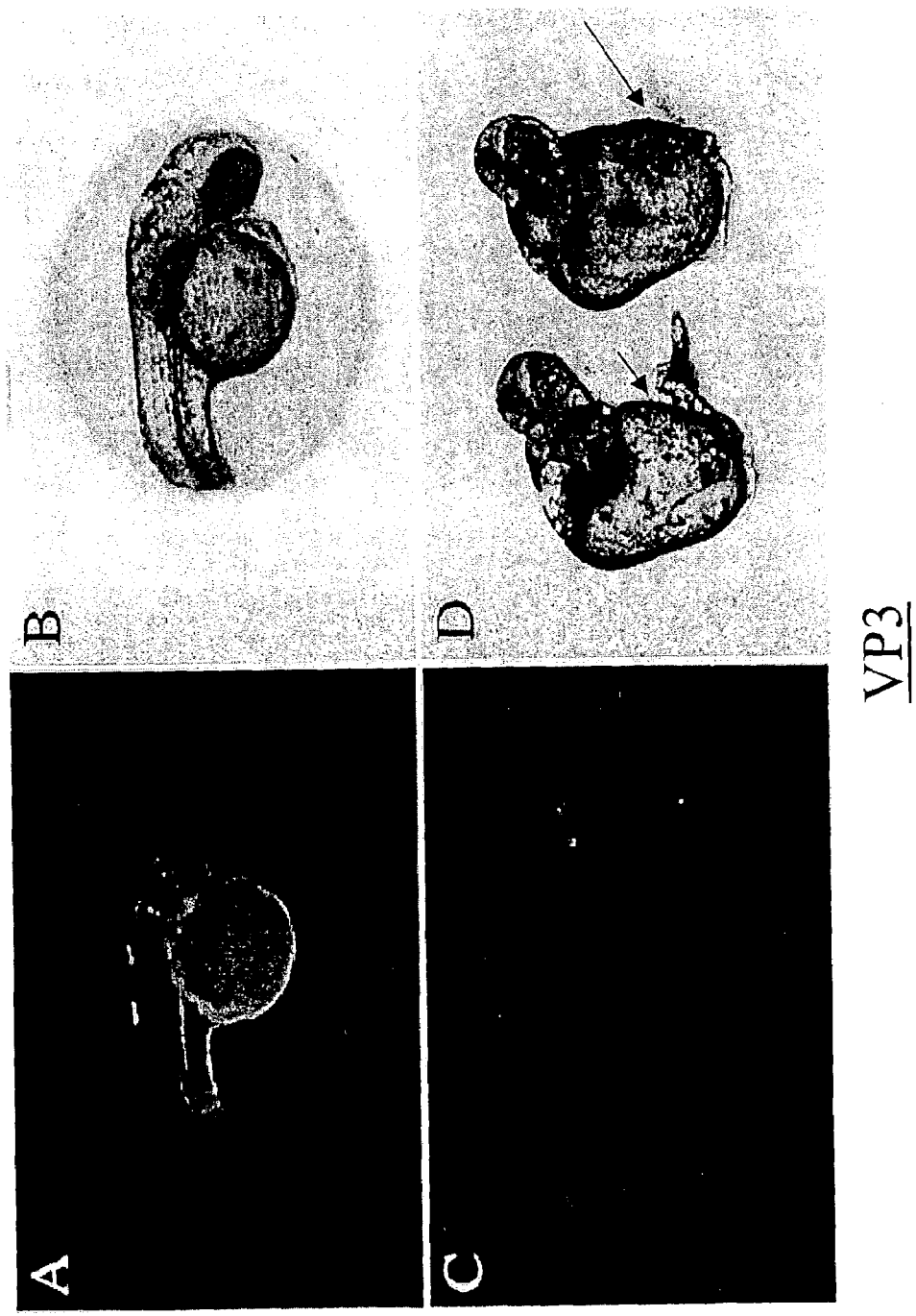

FIG. 20 shows microinjection of pEGFP-C1 (A and B) and pEGFP-VP3 (C and D) into zebrafish embryo for 48 hours. FIGS. 20A and C were fluorescence image (taken under fluorescence microscope); FIGS. 20B and D were brightfield image (taken under light microscope). Severe damages in somite (as shown by arrows) were seen in embryos after microinjected with pEGFP-VP3 for 48 hours.

Figure 21:
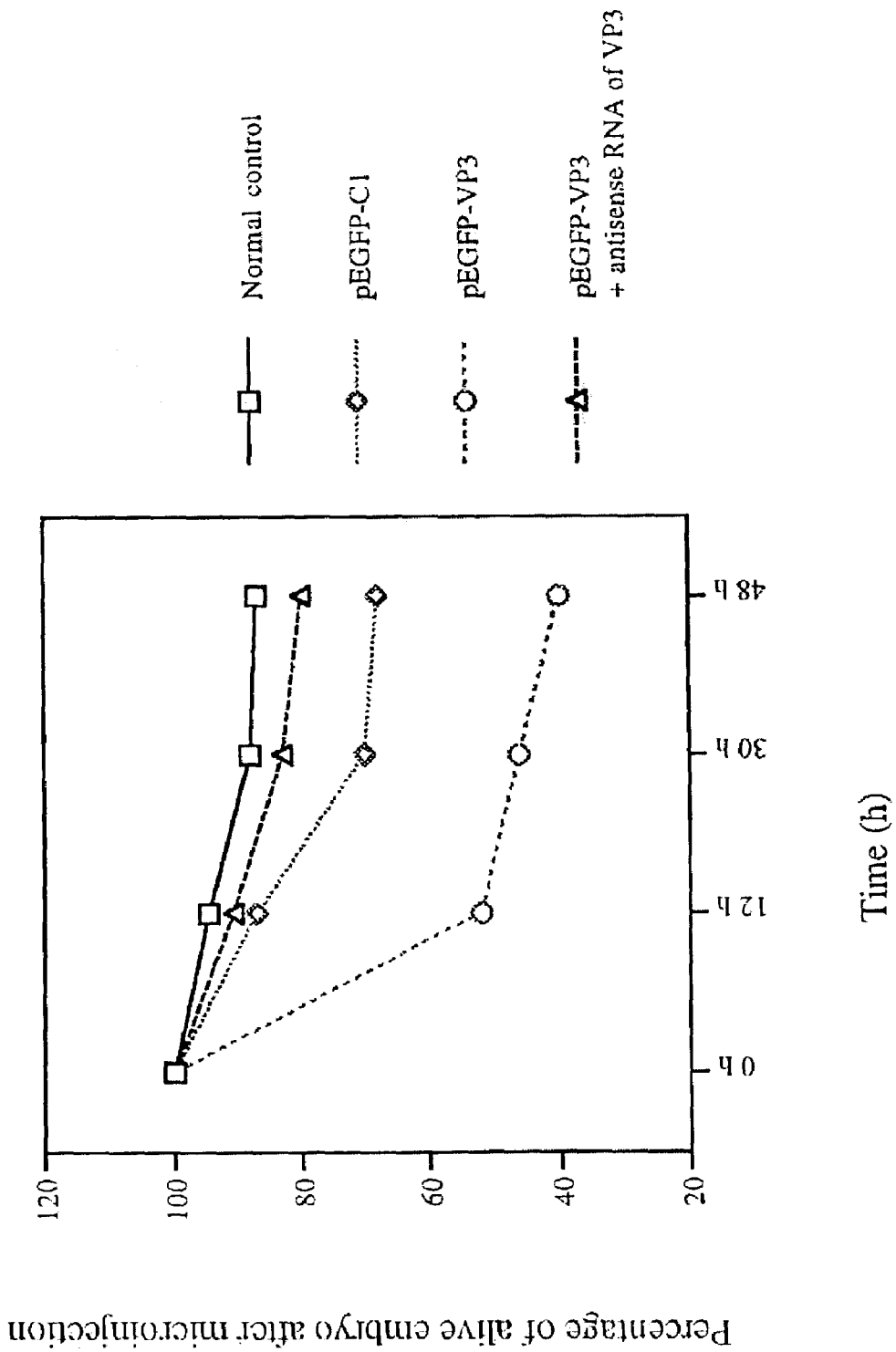

FIG. 21 shows the induction of embryonic death by VP3 and the rescue of embryonic death by VP3 antisense RNA. Survival rate is differences in % of number of alive zebrafish embryos after microinjection of pEGFP-C1, pEGFP-VP3, or pEGFP-VP3 plus antisense RNA of VP3 to the embryos. □ Normal control (88%); pEGFP-C1 (68%); pEGFP-VP3

(42%); pEGFP-VP3+antisense RNA of VP3 (82%, N all more than 100 and repeat three times).

Figure 22:
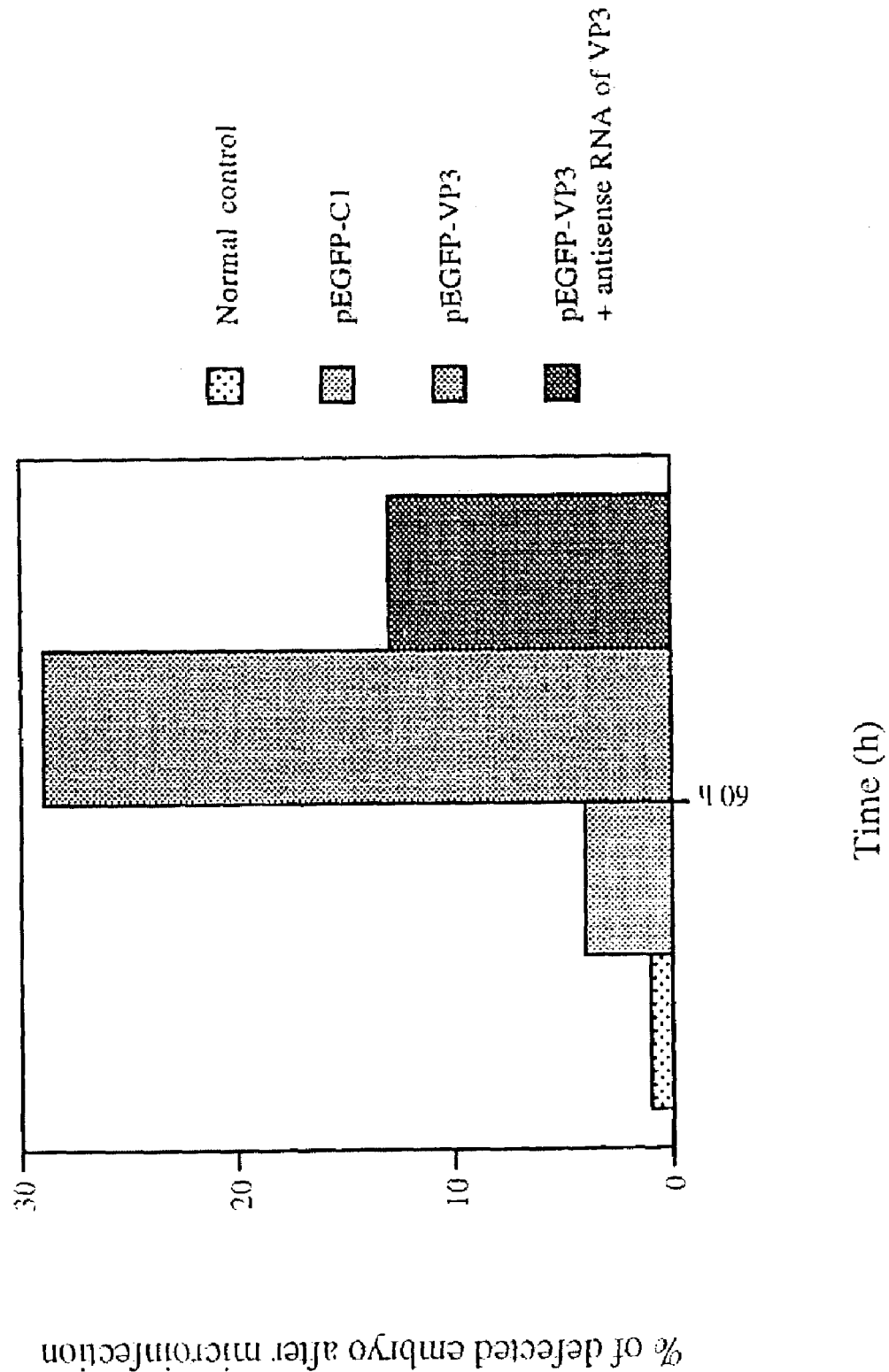

FIG. 22 shows VP3-induced zebrafish embryonic defect and the prevention of VP3-induced zebroyonic defect by VP3 antisense RNA. The bar graph shows the % of defected embryo after microinjection of pEGFP-C1, pEGFP-VP3, or pEGFP-VP3 plus antisense RNA of VP3, to the embryos for 60 hours. Normal control (1%); pEGFP-C1(4%); pEGFP-VP3(12.5%); pEGFP-VP3+antisense RNA of VP3 (29%).

Figure 23:
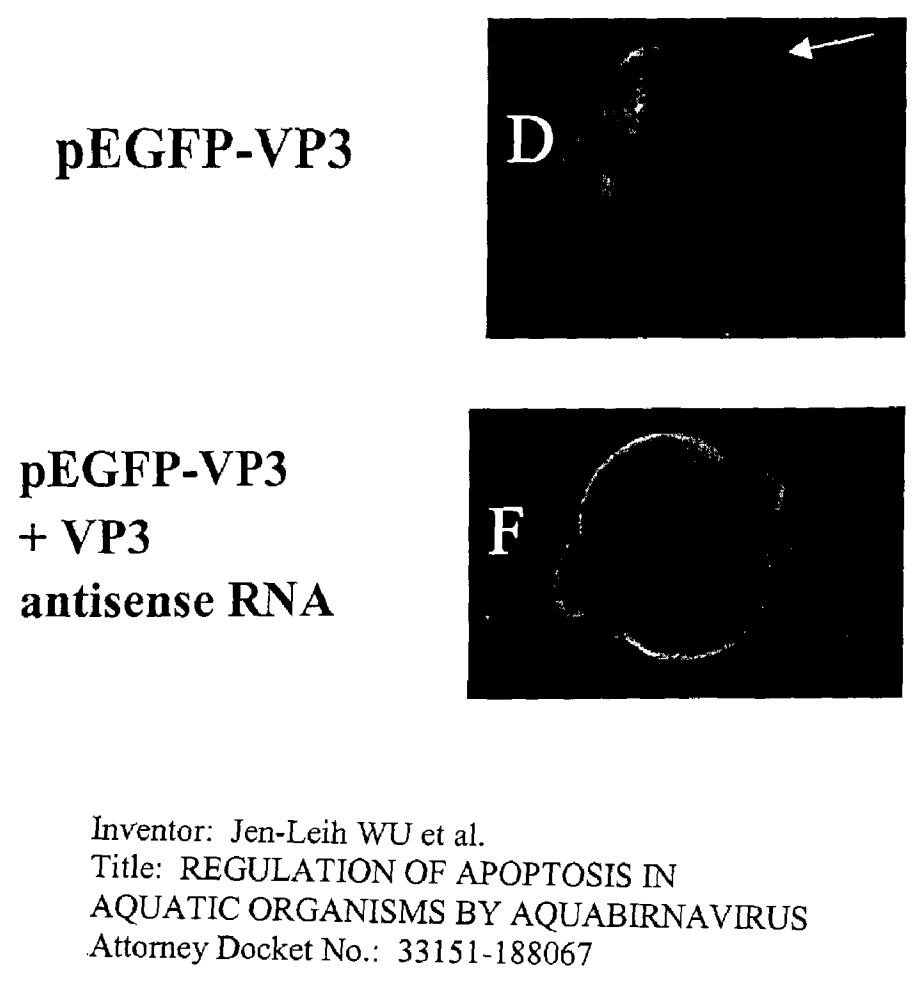

FIG. 23 shows VP3 cell death function blocked by antisense RNA. A composite of two fluoroscence micrographs of zebrafish embryos shown in (D) that was microinjected with pEGFP-VP3 for 12 hours. Arrow shown in (D) indicates materials leaked out of the dead cell. The embryo shown in (F) was microinjected with pEGFP-VP3 and antisense RNA for 12 hours.

Figure 24:
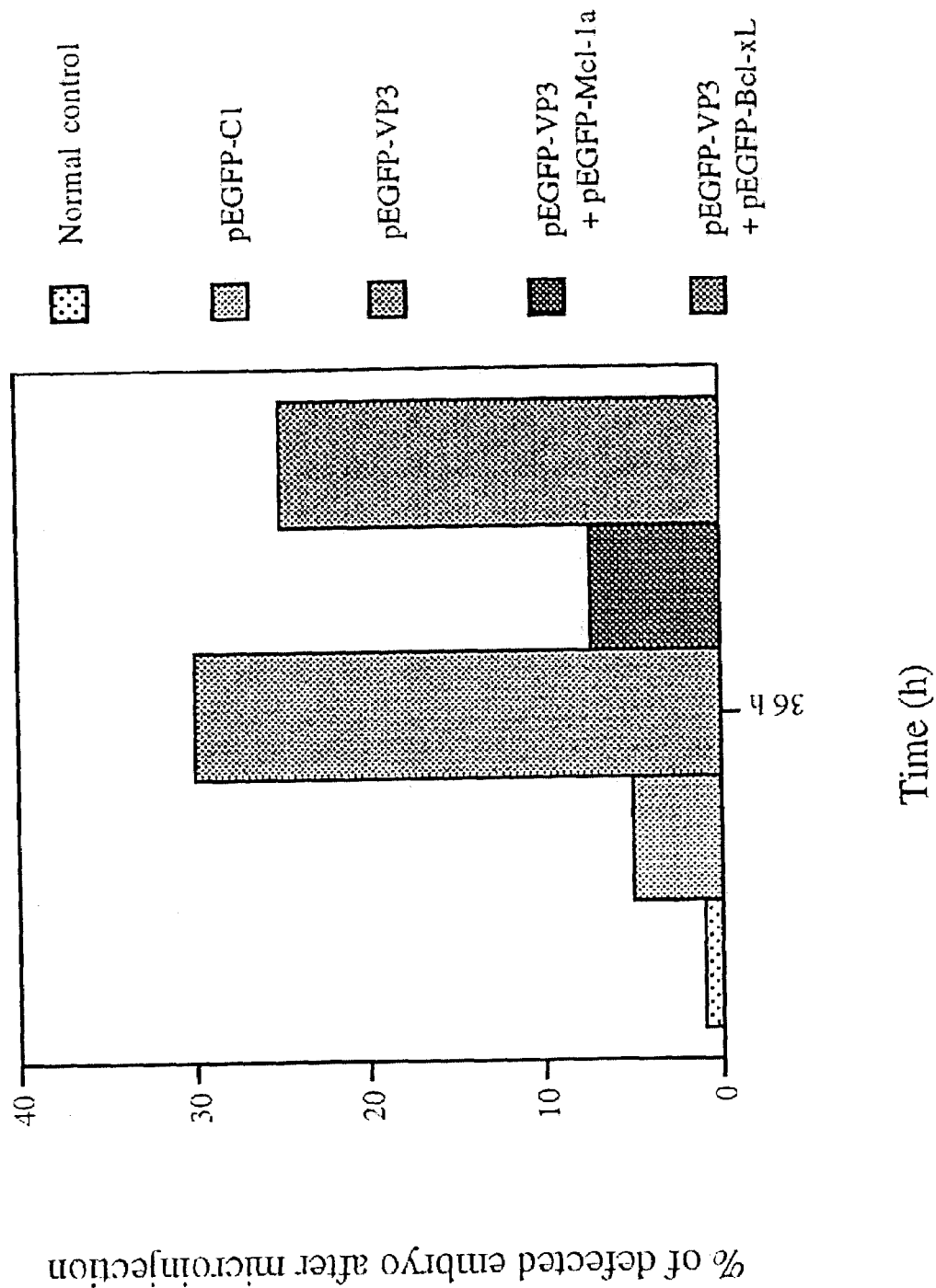

FIG. 24 shows the anti-apoptosis effect of zfMcl-1a (to prevent embryonic defect) during VP3 expression. The bar graph shows the % of defected embryo after microinjection with normal control, pEGFP-C1, pEGFP-VP3, pEGFP-VP3 plus pEGFP-Mcl-1a; or pEGFP-VP-3 plus pEGFP-Bcl-xL for 36 hours. The % of defected embryo after microinjection was as follows: normal control (1%); pEGFP-C1 (5%); pEGFP-VP3 (30%); pEGFP-VP3+pEGFP-Mcl-1a (7.5%); and pEGFP-VP3+pEGFP-Bcl-xL (26%). Both Mcl-1a and Bcl-xL were derived from zebrafish.

Figure 25:
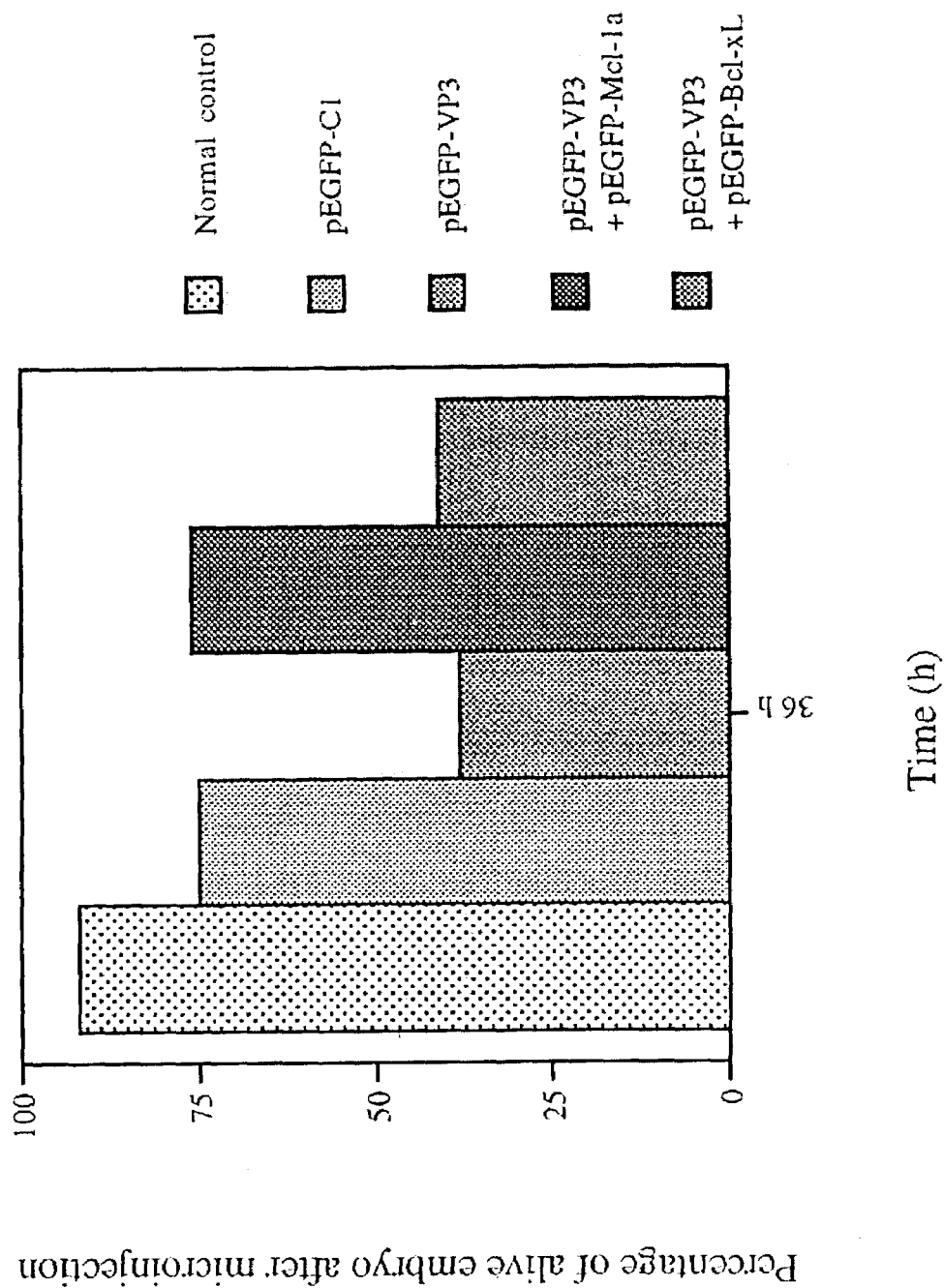

FIG. 25 shows the anti-apoptotic effect of the Bcl-2 family zfMcl-1a on prevention of embryonic death induced by overexpression of VP3. The bar graph shows the % of alive embryos after microinjection with normal control, pEGFP-C1, pEGFP-VP3, pEGFP-VP3 plus pEGFP-Mcl-1a; or pEGFP-VP3 plus pEGFP-Bcl-xL for 36 hours. Normal control (91%); pEGFP-C1 (75%); pEGFP-VP3 (37.5%); pEGFP-VP3+pEGFP-Mcl-1a (76%); pEGFP-VP3+pEGFP-Bcl-xL (39%). Both Mcl-1a and Bcl-xL were derived from zebrafish.

DETAILED DESCRIPTION OF THE INVENTION

Apoptosis is a morphologically distinct cell death that spontaneously occurs in many different tissues under various conditions (Falcieri et al. (1994), Scan. Microsc. 8, 653–666). It occurs in distinctly separated cells and progresses very rapidly, never causing exudative inflammation in tissues. Typically, apoptosis is characterized morphologically by cell shrinkage and hyperchromatic nuclear fragments and biochemically by chromatin cleavage into nucleosomal oligomers.

Infectious pancreatic necrosis virus (IPNV) is the prototype virus of the family Birnaviridae. The virus is capable of infecting a number of different hosts and has a worldwide presence. IPNV is especially susceptible to salmonids, particularly trout, salmon, carp, perch, pike, and eel. The most susceptible fish for IPNV are trout and salmon, such as rainbow trout (*Oncorhynchus mykiss*), brook trout (*Salvelinus fontinolis*), chinook salmon (*Oncorhynchus tshawytscha*), coho salmon (*Oncorhynchus kisutch*), sockeye salmon (*Oncorhynchus nerca*) and Atlantic salmon (*Salmo salar*).

IPNV contains a bisegmented double stranded RNA genome. The larger genome segment A (approximately 3100 bp) of IPNV has two open reading frames: (1) one large 2916 bp ORF encoding a 106 kD polypeptide which can be cleaved into at least three protein; and (2) one overlapping ORF of 444 bp encoding a 17 kD arginine rich polypeptide.

The three proteins encoded by the large ORF include: (1) a 60K to 62K precursor (pVP2) of the 52K to 54K major capsid protein VP2; (2) a 29K non-structural protein (NS); and (3) a 31K minor capsid protein VP3. VP3 is believed to be located internally, associated with the RNA, but may be partly exposed on the surface of the capsid. The localization of the 17 kD polypeptide is not known.

The smaller B segment (approximately 2900 bp) encodes a singe gene product (VP1) with a molecular weight of approximately 94K, presumed to be the viral RNA polymerase. VP1 is present as free polypeptide in the virion and as genome-linked protein, VPg.

IPNV is a contagious disease, which has particular importance of its effects on hatchery raised fish. The virus replicates in the cytoplasm and a single cycle of replication normally takes 16–20 h at 22° C., which results in a characteristic cytopathic effect (CPE).

Recently, Hong et al. (1998), supra, reported that in Chinook salmon embryo (CHSE-214) cells after being infected by IPNV, apoptosis occurred prior to necrosis. Hong et al. were able to demonstrate that during apoptosis, no cell hydration took place, but nuclear and cytoplasmic condensation appeared, which was followed by the formation of numerous membrane-bound cell fragments termed "apoptotic bodies." In addition, in contrast to necrosis, the nuclear organization during apoptosis was completely lost, and profound chromatin rearrangements took place, followed by the formation of a variable number of compact, electron-dense micronuclei. However, despite the extensive nuclear changes, both cytoplasm and organellar components remained intact for some time until the cell underwent secondary necrosis. Only in the final apoptotic stage was the whole cell strongly involved and undergoes a "secondary" necrosis.

In the present invention, further investigation into the apoptotic processes has been carried out. The investigation can be subdivided in two embodiments: (1) Monitoring morphological changes during apoptosis; and (2) Control of cell death via an Mcl-1 dependent pathway.

Embodiment 1: Monitoring Morphological Changes During Apoptosis

Green fluorescent protein (GFP) from the jellyfish *Aequorea victoria* is a revolutionary report molecule for monitoring gene expression and fusion protein localization in vivo or in situ and in real time. One of the most useful aspects of GFP for biological studies is that it can be monitored in living cells. In the present study, a variant type of GFP (EGFP) serves as a marker for visualizing the dynamic apoptotic cell morphological changes and for tracing membrane integrity changes during apoptosis by fluorescence microscopy, as well as for quantitation of the intra- and extracellular release of EGFP during apoptosis by western blotting and fluorometry.

The use of EGFP to study the apoptotic process is illustrated in the following experimental designs, results, and discussion:

(A) Experimental Designs (1) Wild-Type CHSE-214 Cells, CHSE-214-EGFP Cells, and Viruses Chinook salmon embryo cells (CHSE-214) were obtained from American Type Culture Collection (ATCC). Cells were grown at 18° C. as monolayers in plastic tissue culture flasks (Nunc) using Eagle's minimum essential medium (MEM) supplemented with 10% (v/v) fetal calf serum and 25 µg/ml gentamicin. GFP-producing cells were obtained by transfection of CHSE-214 cells with a pEGFP-N1 vector and selection with G418. In these vectors, transcription of insert sequences is driven by the immediate-early promoter of human cytomegalovirus. The coding region contains the EGFP gene, which contains a chromophore mutation which produces fluorescence 35 times more intense than that of wild-type GFP.

The virus isolated, E1-S, a member of the Ab strain of IPNV, was obtained from Japanese eel in Taiwan. E1-S was propagated in CHSE-214 cell monolayers at a multiplicity of infection (MOI) of 0.01 particles per cell. Infected cultures were incubated at 18° C. until an extensive cytopathic effect was observed. The cells were scraped into a tube with the tissue culture medium and chilled on ice, and the cells were then sonicated. This virus stock ($5 \times 10^7$ to $1 \times 10^8$ PFU/ml) was dispensed into 1-ml samples and stored at −70° C. Virus plaque assays were performed on confluent monolayers of CHSE-214 cells that were infected with the virus solution for 1 h at room temperature, overlaid with 0.6% agarose containing 2.5 µg of trypsin per ml, and incubated for 3 days at 18° C. cells were then stained with 1% crystal violet in 20% ethanol (8).

(2) Immunoblotting

About $10^5$ cells per ml were seeded on a 60-mm-diameter petri dish and allowed to grow for more than 20 h. The cell monolayers were rinsed twice with phosphate-buffered saline (PBS), after which they were infected at an MOI of 1 and incubated for 0, 2, 4, 6, 8, 10, 12, and 24 h post infection (p.i.). Uninfected control cells were also incubated for the same periods of time. At the end of each incubation time, the culture medium was aspirated. The cells were washed with PBS and then lysed in 0.3 ml of lysis buffer (10 mM Tris base, 20% glycerol, 10 mM sodium dodecyl sulfate [SDS], 2% β-mercaptoethanol, pH 6.8).

Proteins were separated by SDS-polyacrylamide gel electrophoresis, electroblotted, and subjected to immunodetection as described by Kain et al. (1994), *Bio Techniques*, 17:982–987. Blots were incubated with a 1:7,500 dilution of an immunoglobulin fraction (Clontech) and a 1:1,500 dilution of a peroxidase-labeled goat anti-rabbit conjugate (Amersham). Chemilumine-scence detection was performed in accordance with the instructions provided with the Western Exposure Chemiluminescent Detection System (Amersham). Chemiluminescent signals were imaged by exposure of Kodak XAR-5 film (Eastman Kodak, Rochester, N.Y.). Stripping and reprobing of the Western blot and removal of the primary and secondary antibodies from blot were achieved by incubation in stripping buffer containing 62.5 mM Tris-HCl (pH 6.8), 3.0% (wt/vol) SDS, and 50 mM 1,4-dithiothreitol for 30 min at 55° C. with gentle shaking. The blot was washed three times in PBS containing 0.1% (vol/vol) Tween 20 for 10 min each time and reprobed with antibodies beginning at the membrane blocking step.

Experiments examining the potency of drugs for preventing morphological change and blocking membrane integrity loss and those examining subsequent EGFP retention during virus infection and incubation were carried out as described above, except that extra CHX (10 µg/ml), aprotinin (400 µg/ml), leupeptin (400 µg/ml), genistein (100 µg/ml), tyrphostin (100 µg/ml), and EDTA (2 mM) were added to CHSE-214 cells before virus infection and incubation for 16 h. At the end of the incubation period, cells were harvested and samples were analyzed by Western blotting.

(3) Fluorescence Microscopy

A CHSE-214-EGFP monolayer infected with IPNV (MOI=1) was examined by light and fluorescence microscopy using an Olympus IX70 microscope equipped with a BP450-480 pass excitation filter and a BA515 barrier emission filter for observation of EGFP fluorescence. Photographs were taken with a C-35 AD-4 camera using Kodak Ektachrome 200 film.

(4) DNA Preparation and Gel Electrophoresis

About $10^5$ cells per ml were seeded on a 60-mm-diameter petri dish and allowed to grow for more than 20 h. The cell monolayers received virus at an MOI of 1.0 and were incubated for 8 h. Uninfected control cells were also incubated for 8 h. The two groups were used for DNA fragmentation studies. At the end of incubation, the cells were lysed with lysis buffer (10 mM Tris-HCl, 0.25% Triton X-100, 1 mM EDTA, pH 7.4). After treatment with phenol-chloroform-isoamyl alcohol (25:24:1), the DNA was precipitated in the presence of 0.3 M sodium acetate and cold absolute ethanol at −70° C. for 2 h and then resuspended in 10 mM Tris-HCl (pH 7.4)–1 mM EDTA. Aliquots of 20 µl containing approximately 5 to 10 µg of DNA were then electrophoresed in 1.2% agarose gels for 2 h at 40 V. Gels were stained with ethidium bromide and photographed under UV transillumination.

(5) Scanning Electron Microscopy

Scanning electron microscopy analysis was carried out by cell seeding on a two-chamber slide. CHSE-214 cells were infected with virus at an MOI of 1 and incubated for 0, 4, 8, and 12 h. At the end point, cells were washed twice with PBS and fixed with 2.5% glutaraldehyde in 0.1 M phosphate buffer. Samples were postfixed with $OsO_4$, dehydrated in ethanol, critical point dried, and gold sputtered. A Philips 515 scanning electron microscope was used to examine the specimens.

(6) Immunoelectron Microscopy

CHSE-214-EGFP cells were infected at an MOI of 1. Infected and uninfected control cells were harvested 8 h after infection. Thin-section electron microscopy and immunogold labeling were carried out as described by McNulty et al. (1990), *Avian Pathol.*, 19:67–73. The grids were stained with a 1:1,000 dilution of GFP-specific polyclonal antiserum and a 1:50 dilution of a 15-nm gold-labeled goat anti-rabbit immunoglobulin G conjugate.

(7) Quantitation of EGFP Release by CHSE-214-EGFP Cells

Cellular EGFP and culture medium EGFP protein samples were prepared for assay in EGFP release experiments. About $10^5$ cells per ml were seeded on a 60-mm petri dish for more than 20 h. Cell monolayers were rinsed twice with PBS and then cultured in 3 ml of 10% FCS-containing MEM. Uninfected cells used as a normal control and cells that received virus at an MOI of 1 were incubated for 0. 2, 4, 6, 8, 10, 12, and 24 h p.i. At the end of each incubation period, the culture medium was collected to determine the concentration of retained EGFP. Cells were washed with PBS and then lysed in 0.3 ml of lysis buffer (10 mM Tris base, 20% glycerol, 10 mM SDS, 2% β-mercaptoethanot, pH 6.8).

The assay procedure was as follows. First, recombinant GFP purchased from Clontech was used as the standard. The GFP standard was diluted from 1 µg/0.1 ml to 0.001 µg/0.1 ml with 10% FCS-containing MEM. Second, 5 µg of lysed cells per sample was diluted with 10% FCS-containing MEM to a final volume of 100 µl. Third, the supernatant was assayed, and 30 µg of supernatant per sample was diluted with 10% FCS-containing MEM to a final volume of 100 µl. Protein concentration was determined by the dye-binding method of Bradford using a commercially available kit (Bio-Rad, Richmond, Calif.) with bovine serum as the standard. Fourth, the fluorescence intensity of three group samples was counted by a Fluorolite 1000 (DYNEX). The EGFP concentrations of the lysed cells and supernatant were evaluated by comparing them with that of the GFP standard by using a Fluorolite 1000 and dividing by 35.

(B) Results (1) Visualization of Dynamic Morphological Changes by EGFP

Figure 1:
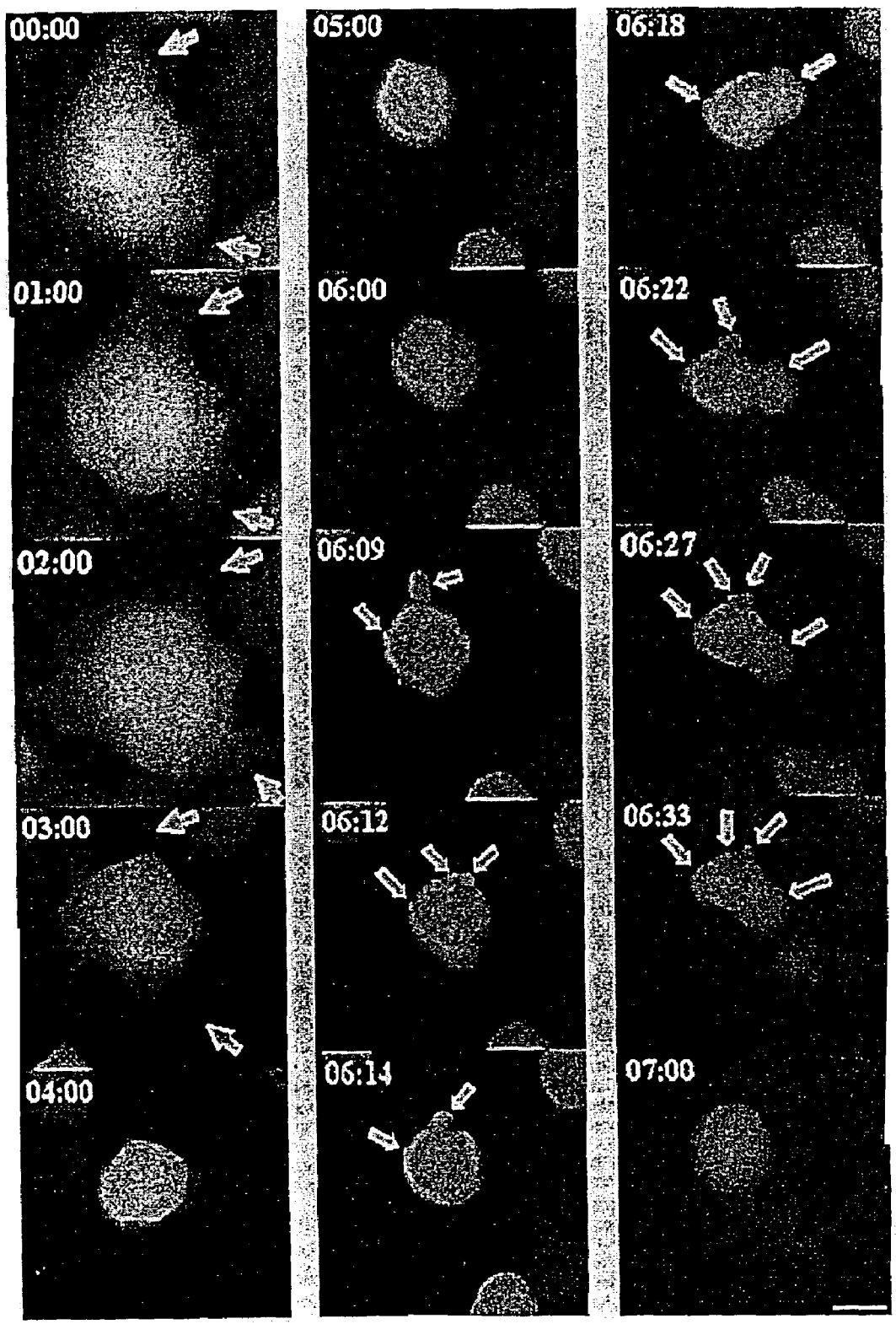

FIG. 1 shows the sequential morphological changes that occurred in CHSE-214-EGFP cells during virus infection (MOI=1). These events were divided into three stages. First (early stage), detachment of the CHSE-214-EGFP cell matrix was initiated between 0 and 3 h p.i. Second (middle stage), the whole cell was rounded up and appeared morphologically more compact. In this period (3 to 6 h p.i.), the cell volume decreased to one-third of its original size and the fluorescence intensity was enhanced. In the third (pre-late) stage, the cells at 6 to 7 h P.i. quickly underwent severe morphological changes. Membrane vesicles (MV) were formed from the plasma membrane, and these vesicles eventually blebbed and finally pinched off from the cell membrane.

(2) Induction of Internucleosomal Cleavage by IPNV in CHSE-214-EGFP Cell

Figure 2:
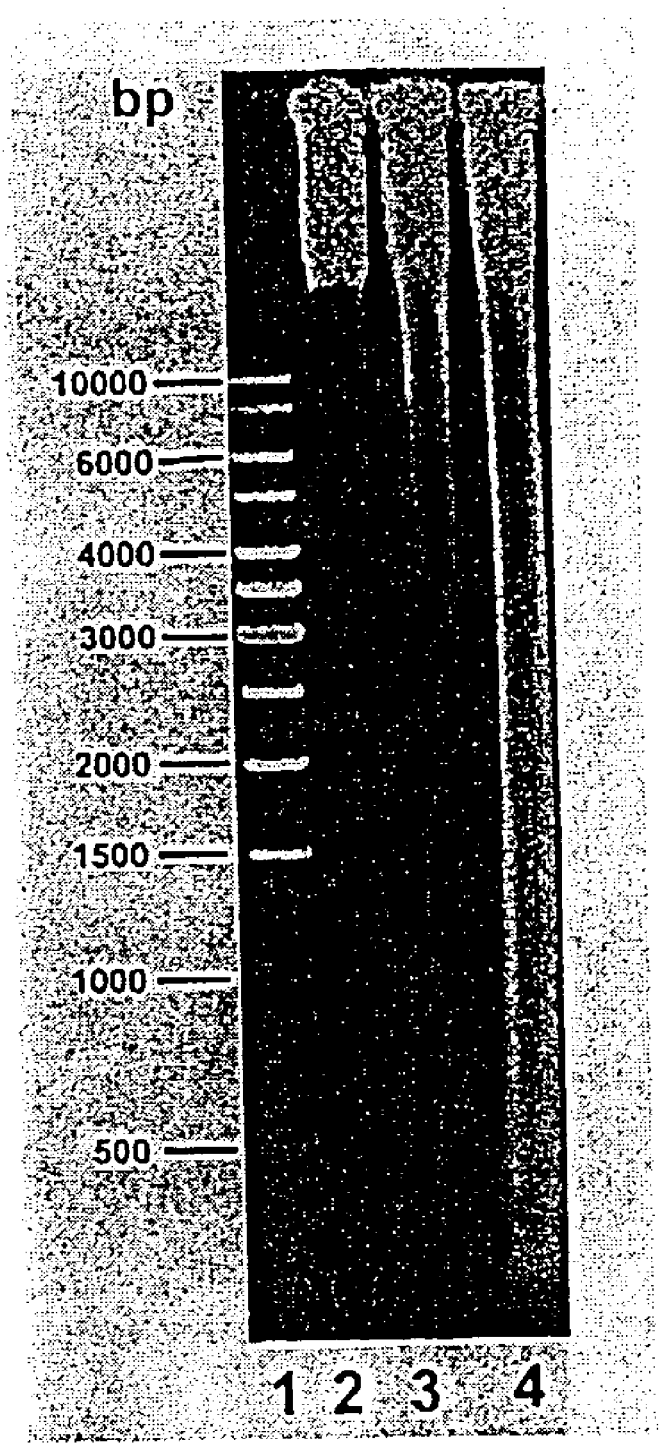

The effect of IPNV infection on host DNA in CHSE-214-EGFP cells was examined by agarose gel electrophoresis. Virus (MOI=1) infected cells were examined for evidence of internucleosomal fragmentation. DNA fragmentation is a well-defined biochemical marker of apoptosis. FIG. 2 shows the results of agarose gel electrophoresis which demonstrates that intense internucleosomal fragmentation of DNA, a pattern highly specific to apoptosis, occurred in CHSE-214-EGFP cells infected with IPNV. The IPNV induced DNA fragmentation at 8 h p.i. is shown in FIG. 2, lane 4. The negative control which showed no DNA fragmentation at 0 and 8 h of incubation is shown in FIG. 2, lanes 2 and 3. Lane 1 of FIG. 1 shows molecular weight markers that ranged from 500 bp to 1 kb (from MBI Fermantas Inc.).

Figure 3:
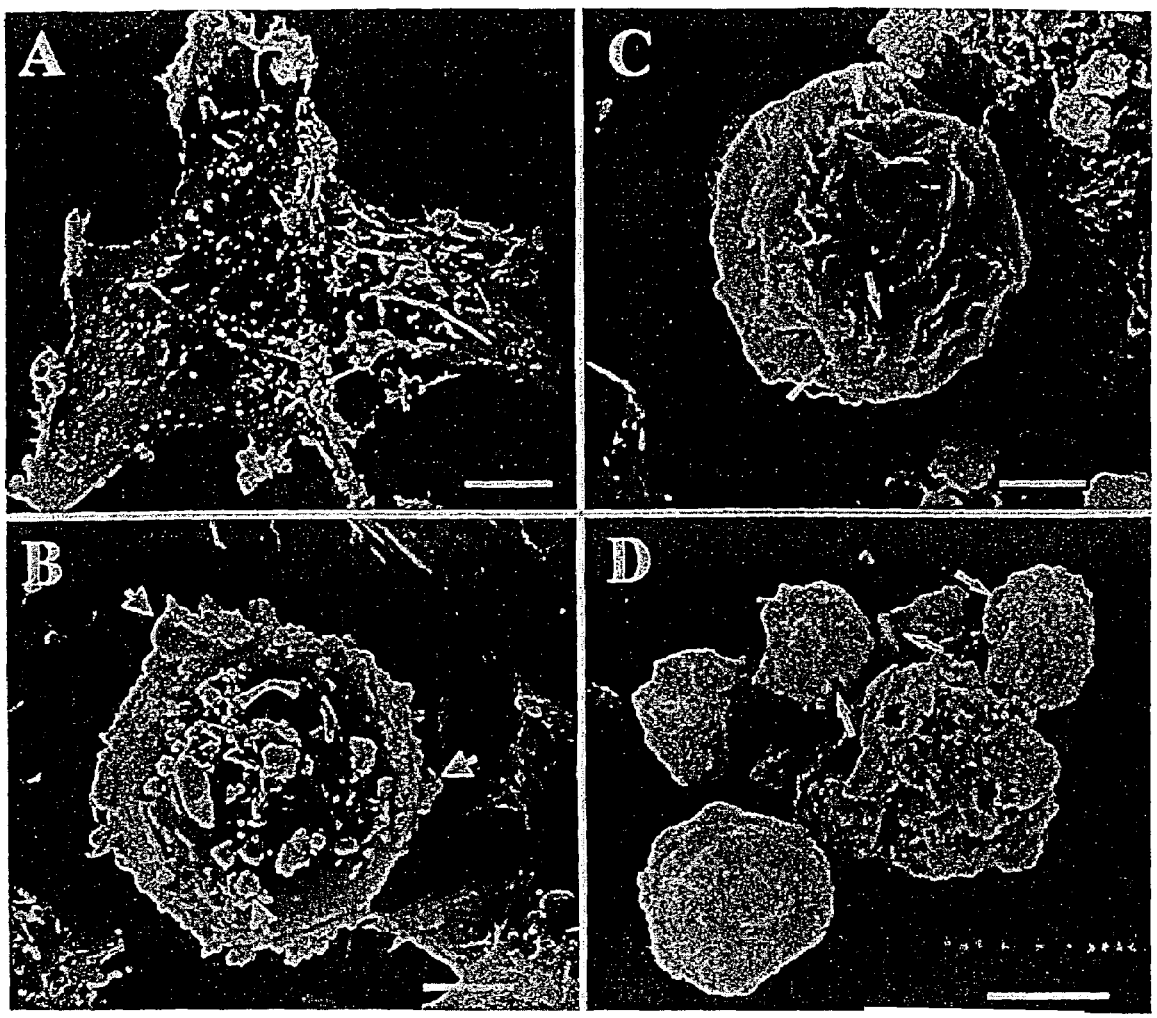

(3) Ultrastructural Morphology Changes in IPNV-Infected CHSE-214 Cells Detected by Scanning Electron Microscopy Apoptosis induces characteristic morphological changes in cells, such as condensation and fragmentation of the nucleus, as well as loss of cytoplasm. To substantiate further that IPNV-infected cells had undergone nontypical apoptotic morphological changes such as membrane integrity changed, negative control and IPNV-infected CHSE-214 cells were harvested and processed for scanning electron microscopy as shown in FIG. 3. Negative control cells are shown in FIG. 3A. IPNV-infected CHSE-214 cells at 8 h p.i. displayed detachment, cell rounding, and blebbing of membrane vesicles (MV) from the plasma membrane at the pre-late stage of apoptosis (20%; $P<0.05$), as shown in FIG. 3B. Middle-late-stage apoptotic cells (23%; $P<0.05$) are shown in FIG. 3C. The cell membrane appears shrunken, and holes are present in the plasma membrane. The hole sizes ranged from 0.39 to 0.78 $\mu$m with about 10 to 20 holes per cell. A late-stage apoptotic cell (2%; $P<0.05$) is shown in FIG. 3D with the small holes still on the surface of the late-apoptotic cell.

Figure 4:
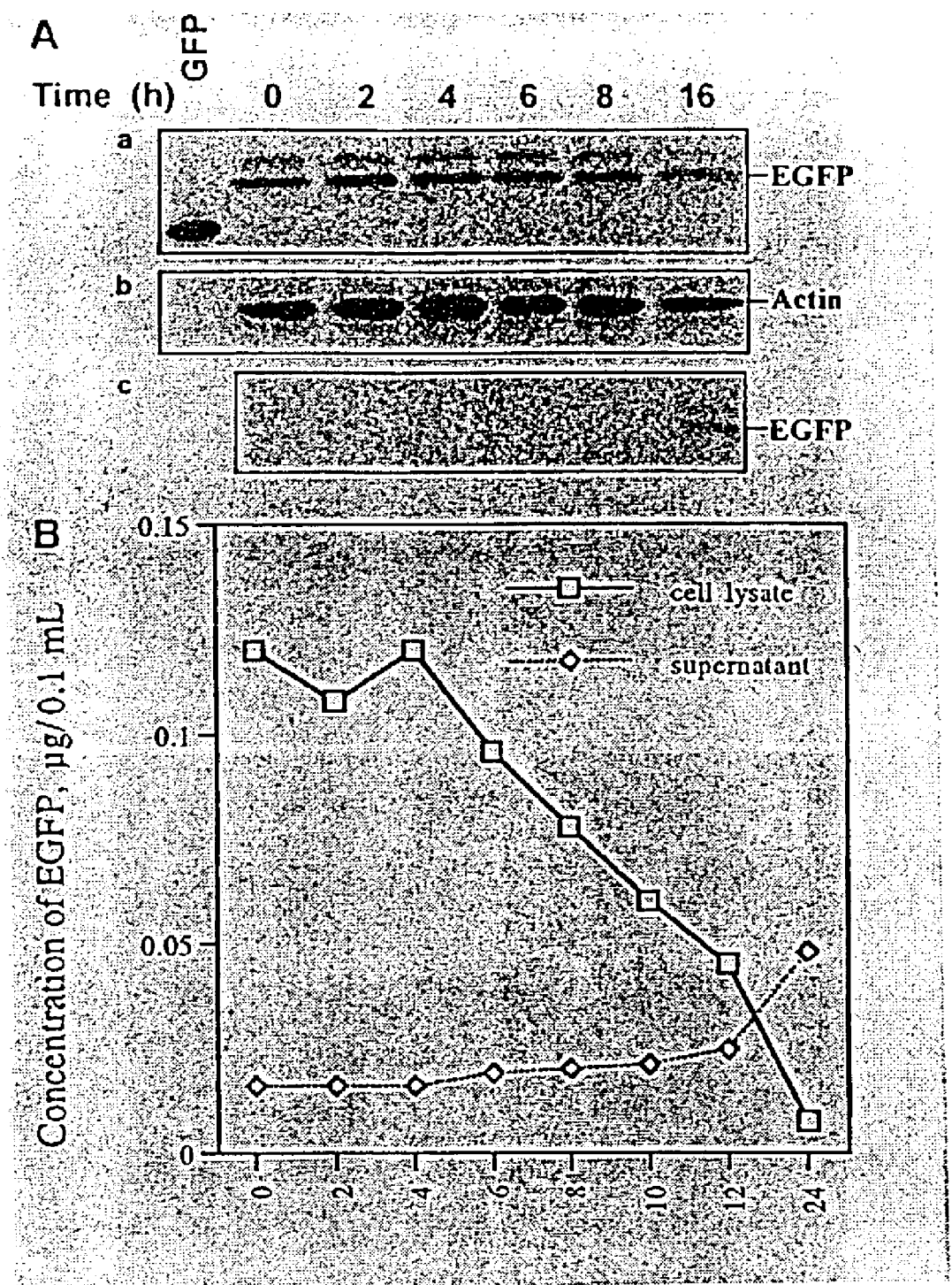

(4) EGFP Release is Prevented by Protein Synthesis Inhibitor and Tyrosine Kinase Inhibitor In EGFP release experiments, EGFP was used to monitor the integrity of the plasma membrane during apoptosis. As described in (3) above, small holes appeared in middle-late-stage apoptotic cells (FIG. 3C). It is possible that intracellular material might leak out of these small holes to the extracellular region before secondary necrosis. The use of EGFP to monitor the integrity of the plasma membrane of IPNV-infected CHSE-214-EGFP cells is shown in FIG. 4. The EGFP release Western blot assay result is shown in FIG. 4A. FIG. 4A, part a, shows that the amount ot GFP decreased, especially between 8 and 16 h p.i. The internal control, actin protein, is shown in FIG. 4A, part b. Detection of the EGFP released from the intracellular to the extracellular region during IPNV infection is shown in FIG. 4A, part c. The increase of GFP release began between 8 and 16 h p.i., which is consistent with FIG. 4A, part a. These data indicate that the membrane integrity changed quickly at the middle-late apoptotic stage. The fluorometric EGFP release assay results are shown in FIG. 4B. The open squares show that the intracellular amount of EGFP sharply decreased from 6 to 24 h p.i. but that the largest release of EGFP occurred between 12 and 24 h p.i. The open diamonds show that the extracellular amount of EGFP increased between 6 and 24 h p.i., which matches the intracellular data described above. EGFP was also used as a protein indicator to directly probe membrane integrity by immunoelectron microscopy. Normal CHSE-214-EGFP cells used as controls are shown in FIG. 5A. FIG. 5B shows that the small vesicle escaped from the membrane hole at the pre-late apoptotic cell stage and that the vesicle contains the same EGFP labeled by an anti-GFP polyclonal antibody-gold complex.

Figure 6:
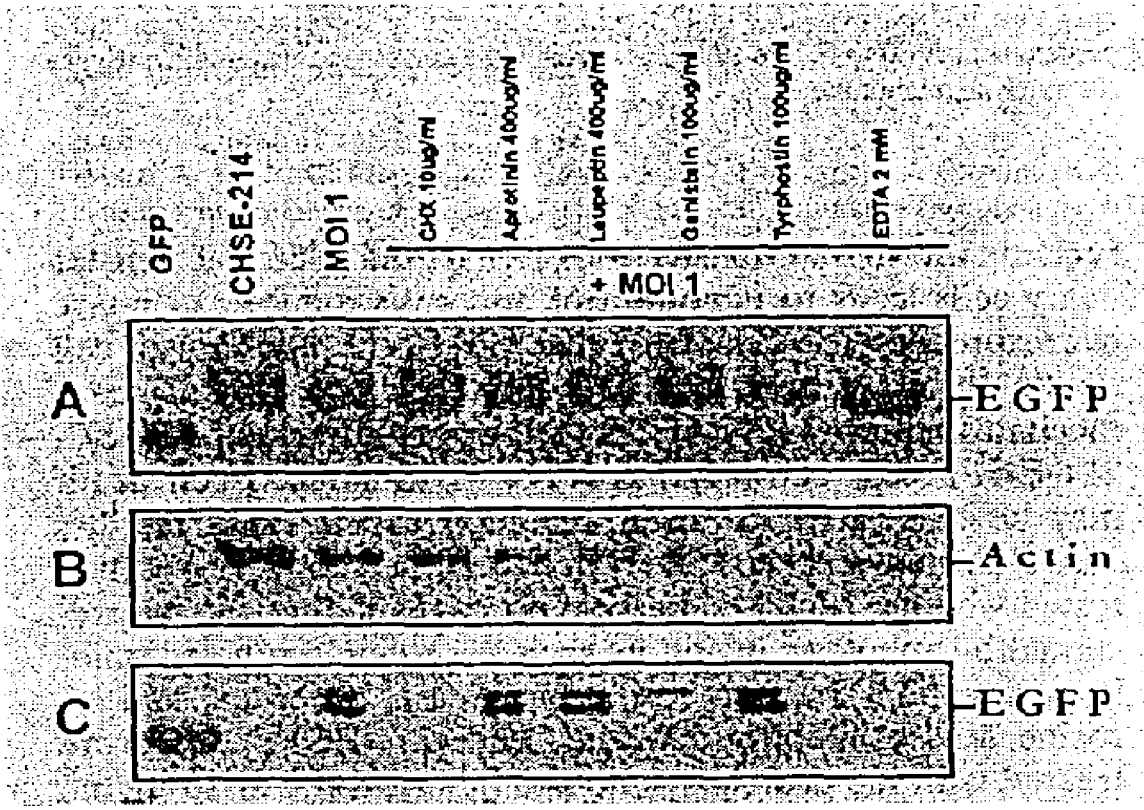

Drugs, including the protein synthesis inhibitor cycloheximide (CHX), the serine proteinase inhibitors aprotinin and leupeptin, the tyrosine kinase inhibitors genistein and tyrphostin, and the cation chelator EDTA, were used before IPNV infection to test the viability of these drugs on preventing membrane integrity change. Some of the drugs, such as CHX at 10 $\mu$g/ml and 2 mM EDTA, completely prevented EGFP release, and genistein at 100 $\mu$g/ml partially prevented EGFP release (as shown in FIG. 6A) to the extra-cellular region (as shown in FIG. 6C). The serine proteinase inhibitors aprotinin (400 $\mu$g/ml) and leupeptin (400 $\mu$g/ml) (FIG. 6C, lanes 5 and 6, respectively) and the tyrosine kinase inhibitor tyrphostin (100 $\mu$g/ml) (FIG. 6C, lane 8) did not prevent EGFP release. The internal control, actin protein, is shown in FIG. 6B for quantitation of protein loading per sample.

(C) Discussion

The present invention provides the first evidence that GFP can be used to sequentially monitor apoptotic morphological changes in living cells. GFP is stable and species independent and can be monitored noninvasively in living cells. However, working with GFP raises practical problems. One such problem, common in fluorescence microscopy of live cells, is that of phototoxicity, which is thought to be caused mainly by fluorophore-mediated generation of free radicals. Fortunately, the introduction of mutant GFPs with higher quantum efficiencies, lower-energy excitation spectra, and better temperature stability has been advantageous and has significantly widened the applicability of GFP to the study of proteins of low abundance.

For the purposes of studying the changes in membrane integrity after IPNV infection, a clone with strong fluorescence intensity and normal morphology, CHSE-214-EGFP, was selected and subcloned as a cell line for experiments as shown in FIG. 1. This clone uses a variant type of GFP, EGFP, as a probe. The use of EGFP to study the morphological changes during apoptosis clearly has advantages over GFP because EGFP produces fluorescence 35 times more intense than GFP. The clones with lower fluorescence intensity did not produce a good image in sequential morphology studies.

Figure 5:
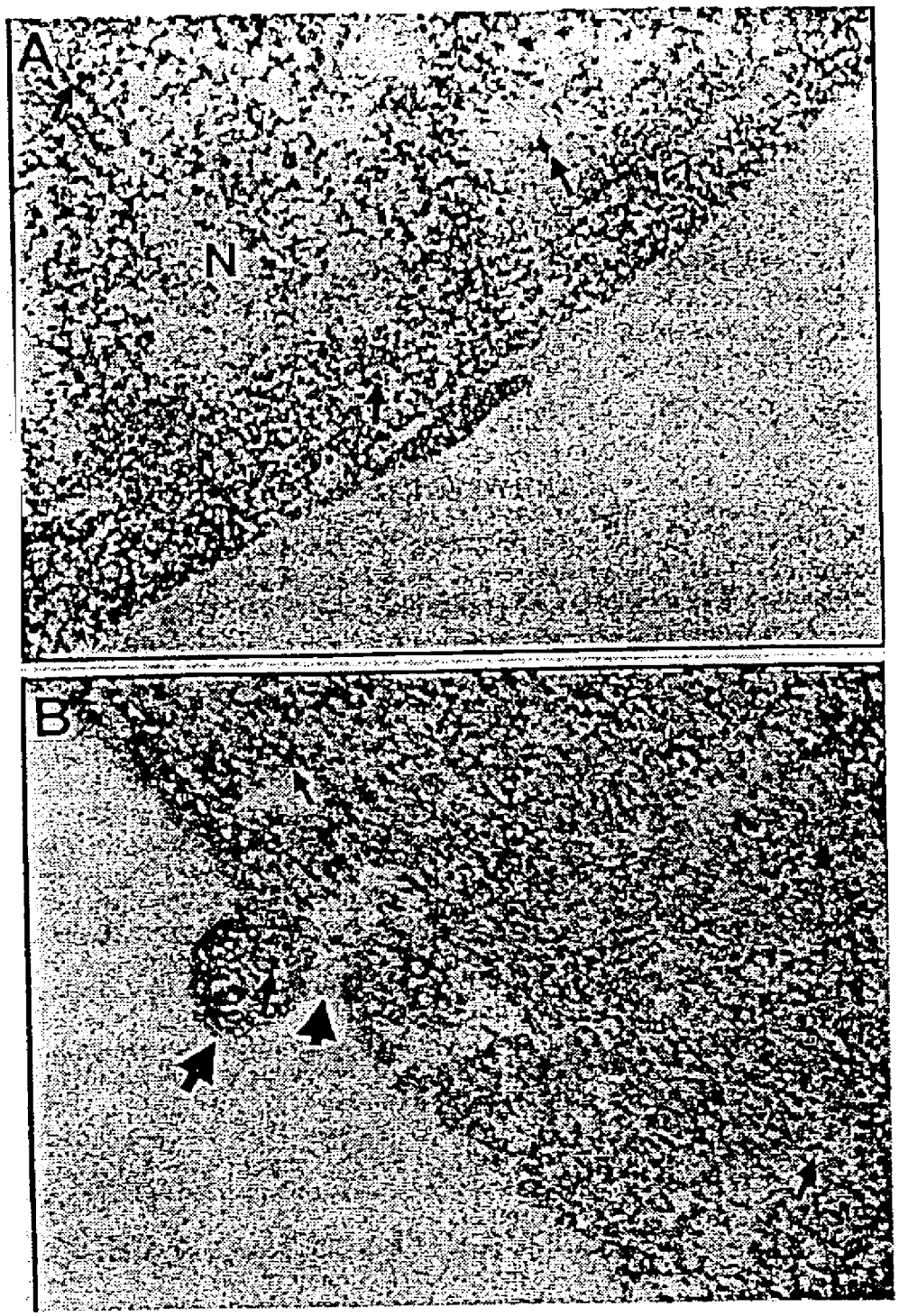

The cloned CHSE-214-EGFP cells were expressed with EGFP (32.5 kDa; as shown in FIG. 4A, lane 2), which is larger in molecular size than wild-type GFP (27 kDa; as shown in FIG. 4A, lane 1). But other characteristics of EGFP are similar to GFP. For example, GFP is fluorescent either as a monomer or as a dimer. The ratio of monomeric to dimeric forms depends on the protein concentration and the environment. EGFP was also found in both control cells and IPNV-infected cells either as a monomer or as a dimer (as shown in FIG. 5). In fact, a doublet EGFP was found in the released EGFP, as shown in FIG. 4A (part c, lane 6) and 6C.

The results of using EGFP to monitor the dynamic morphological changes in CHSE-214-EGFP cells infected with IPNV are shown in FIG. 1. The series of events can be briefly divided into four stages: (i) the early apoptotic stage (0 to 3 h p.i.), (ii) the middle apoptotic stage (3 to 6 h p.i.), (iii) the pre-late apoptotic stage (6 to 7 h p.i.), and (iv) the postapoptotic necrosis stage (after 7 h p.i.). The morphological changes in apoptotic cells observed include cell detachment. rounding up, formation of MV, pinched off MV floating away in the culture medium, and finally, postapoptotic necrosis.

Figure 7:
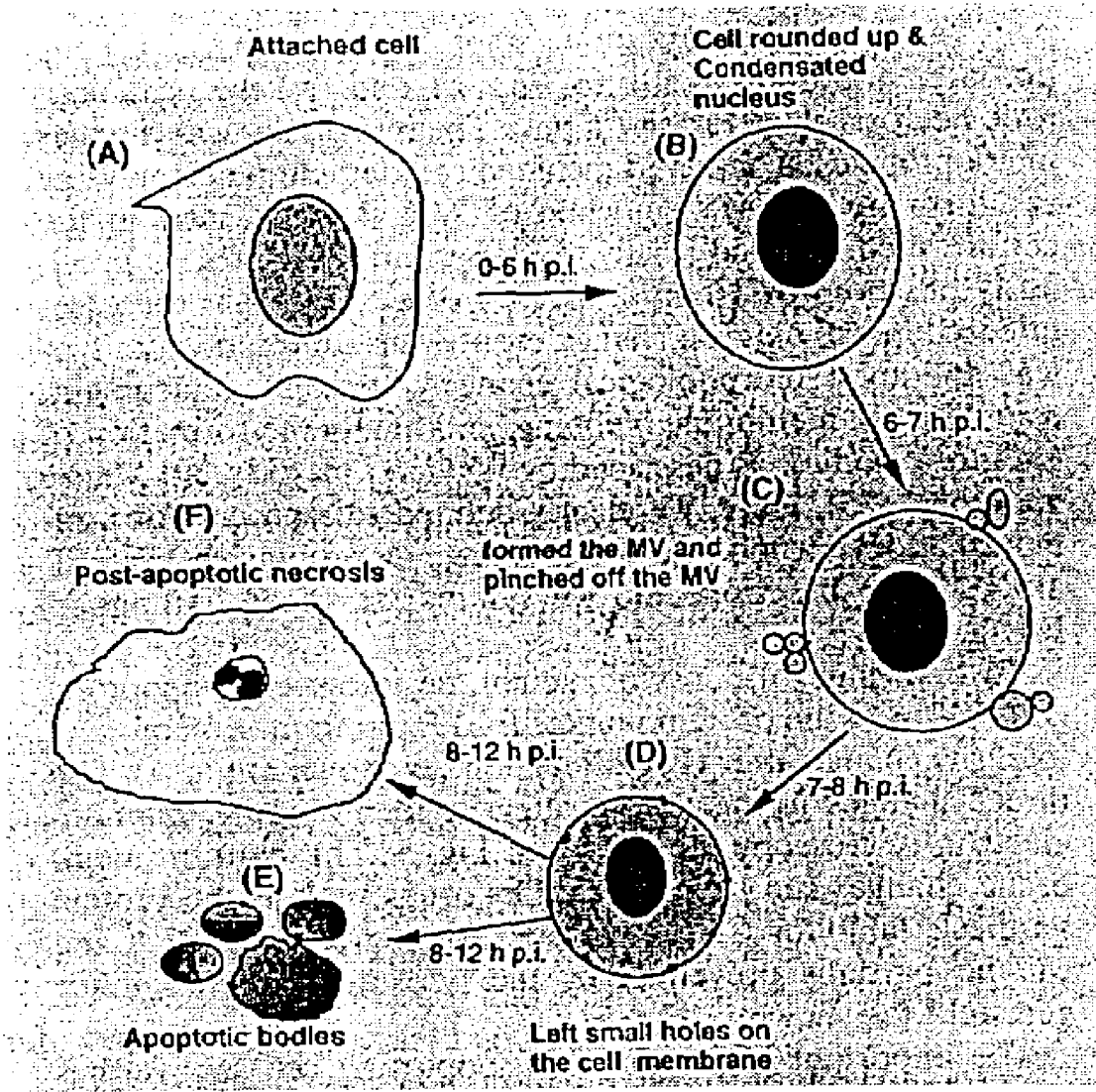

The sequential morphological change events were different from typical apoptotic morphological changes, which are characterized as detachment, rounding up, membrane blebbing, and finally the formation of apoptotic bodies, as described by Wyllie et al. supra. The apoptotic process of CHSE-214 after IPNV infection is clearly defined as a "non-typical apoptotic morphological change" as summarized in FIG. 7, which include all of the typical characteristics of apoptosis, namely, DNA fragmentation, cell detachment and rounding up (FIG. 7A-B), membrane blebbing and formation of membrane vesicles (MV) (FIG. 7C), and MV pinching off from the membrane which left small holes on the cell membrane (FIG. 7D). However, at the late apoptotic stage, in addition to the formation of apoptotic bodies (FIG. 7E) as in the typical apoptosis, the apoptotitc cells can undergo post-apoptotic necrosis (FIG. 7F) which is characterized by the condensed chromatin enclosed by the nuclear membrane.

Embodiment 2. Control of Cell Death Via An Mcl-1 Dependent Pathway

Mcl-1 belongs to the Bcl-2 family, which is known as the "apoptosis-inhibiting protein". The founding member of this family is the bcl-2 protooncogene which was initially isolated from a follicular lymphoma (Bakhshi et al. (1985), *Cell* 41:889–906). Mcl-1 was originally identified from the differentiating human myeloid leukemia cell line ML-1. Its expression was found to increase early in the induction or "programming" of differentiation of ML-1 cells before the appearance of differentiation markers. The coding region of mcl-1 was sequenced and found to have a pronounced region of sequence homology to bcl-2 in the carboxyl-terminal region (Kozopas et al. (1993), supra). Unlike bcl-2, mcl-1 contains a strong PEST sequence (enriched in proline, glutamic acid, serine and threonine) which is present in a variety of proteins that undergo rapid turnover. Overexpression of exogenously introduced mcl-1 has been shown to cause a prolongation of viability under conditions that normally cause apoptotic cell death, such as exposure to cytotoxic agents (e.g., the chemotherapeutic agent etoposide, calcium ionophore, or UV irradiation) or the withdrawal of required growth factors (Zhou et al. (1997), *Blood* 89:630–643).

Although Mcl-1 has been studied in mammalian cells, no such study has been conducted in aquatic cells. In addition, the present invention is the first to study the down regulation of Mcl-1 protein expression by viral infection. The experimental designs, results, and discussion of this embodiment are illustrated as follows:

(A) Experimental Design (1). CHSE-214 and Viruses

Chinook salmon embryo cells (CHSE-214) and E1-S of IPN virus Ab strain were prepared according to (1) of the Experimental Design in Embodiment 1, supra.

(2). Scanning Electron Microscopy

The scanning electron microscopy was prepared according to (5) of the Experimental Design of Embodiment 1, supra.

(3). DNA Preparation and Gel Electrophoresis

The DNA preparation and agarose gel electrophoresis were prepared according to (4) of the Experimental Design of the Embodiment 1, supra.

(4). Immunoblotting

About $10^5$ cells/ml were seeded on a 60-mm. petri dish for growth for more than 20 h. Monolayers were rinsed twice with phosphate-buffered saline (PBS). Control cells or cells that received virus at a MOI of 1 were incubated for 0, 2, 4, 6, 8, 10 and 24 h. At the end of each incubation time the culture medium was aspirated. The cells were washed with PBS and then lysed in 0.3 nil lysis buffer [10 mM Tris base, 20% glycerol, 10 mM sodium dodecyl sulfate (SDS), 2% β-mercaptoethanol (P-ME), pH 6.8].

Proteins were separated by SDS-polyacrylamide gel electrophoresis (Laemmli, 1970), electroblotted, and subjected to immunodetection as described by Kain et al. (1994). Blots were incubated with a 1:1500 dilution of anti-human Mcl-1 polyclonal antibodies (Pharmingen) or a 1:7500 dilution of a peroxidase-labeled goat anti-rabbit conjugate (Amershan). Chemi-luminescent detection was performed according to the instructions provided with the Western Exposure Chemi-luminescent Dectection System (Amershan). Chemiluminescent signals were imaged by exposure to Kodak XAR-5 film (Eastman Kodak, Rochester, N.Y., USA). Primary (Mcl-1) and secondary antibodies (peroxidase-labeled goat anti-rabbit conjugate) were stripped from blots by incubation in stripping buffer containing 62.5 mM Tris-HCI (pH 6.8), 3.0% (w/v) SDS and 50 mM 1,4-dithiothreitol for 30 min at 55° C. with gentle shaking. The blots were then washed four times for 10 min each time in PBS containing 0.1% (v/v) Tween 20 and reprobed with mouse actin monoclonal antibody (1/1500, Chemicon) and a 1:7500 dilution of a peroxidase-labeled sheep anti-mouse conjugate (Amersham).

The potent drugs on effect of blockage on viral protein expression experiment, the cell preparation was as described above except that extra, cycloheximide (10µ4 g/ml), aprotinin (400 µg/ml), leupeptin (400 µg/ml), genistein (100 µg/ml), tryphostin (100 µg/ml) and EDTA (2 mM) were added to 3 nil of MEM medium on CHSE-214 cells before virus infection and incubation for 16 h. At the end of the incubation period, cells were harvested and the samples were analyzed by Western blot method.

(B) Results (1). Ultrastructure Morphological Changes in CHSE-214 Cells with IPNV Infection by Scanning Electron Microscopy Apoptosis induces characteristic morphological changes in cells, such as condensation and fragmentation of the nucleus as well as loss of cytoplasm (Wyllie et al. (1984), supra). To substantiate that IPNV-infected cells had undergone apoptosis, negative control and IPNV-infected cells were harvested and processed for scanning electron microscopy. Normal negative control cells are shown in FIG. 8A. IPNV-infected CHSE-214 cells displaying detachment and blebbing of the plasma membrane are shown in FIG. 8B.

(2). Induction of Internucleosomal Cleavage by IPNV in CHSE-214 Cells

Figure 9:
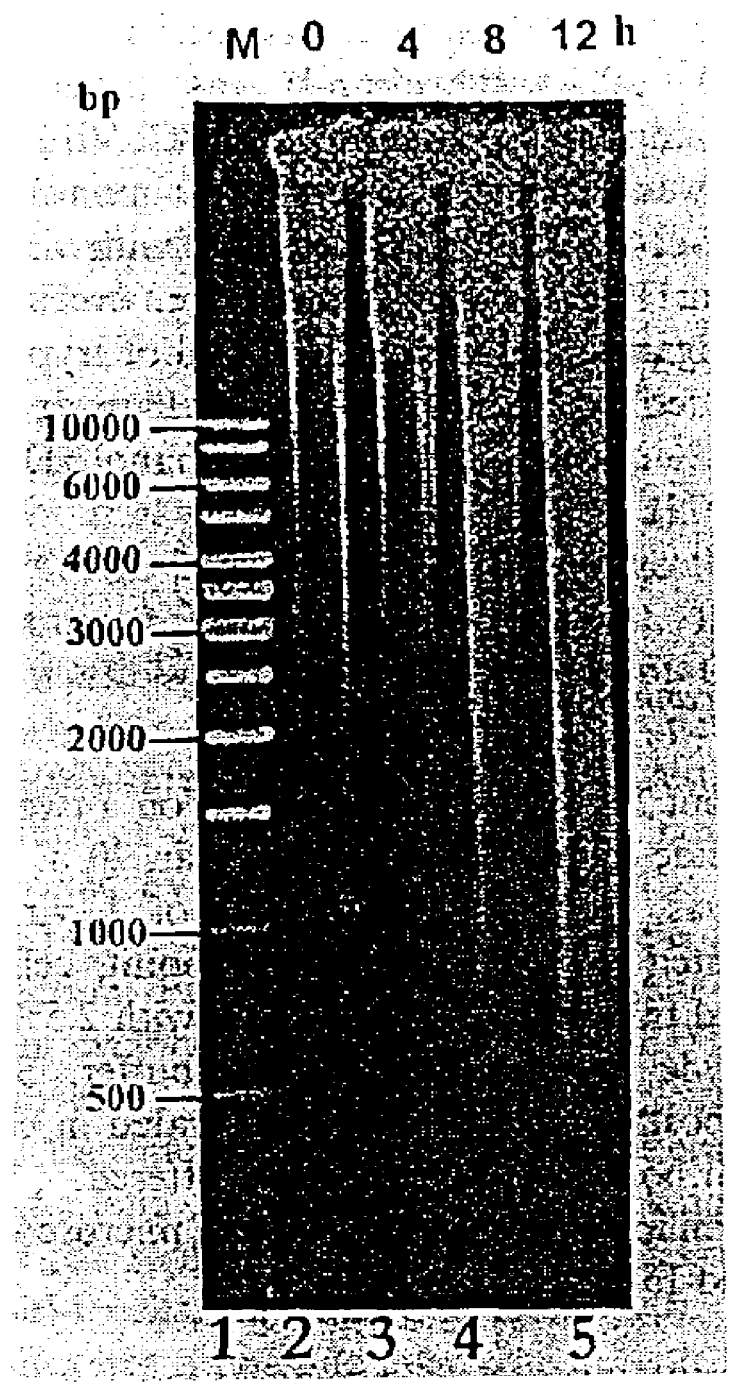

DNA fragmentation is a well-defined biochemical marker of apoptosis. E1-S of IPN virus Ab strain (MOI of 1) infected cells were examined for evidence of internucleosomal fragmentation. Intense internucleosomal fragmentation of DNA, a pattern highly specific to apoptosis, was observed in CHSE-214 cells infected with IPNV (FIG. 9). The IPNV induced DNA fragmentation at 8 h and 12 h postinfection was identified by gel electrophoresis (FIG. 9, lanes 4 and 5). The gel of the negative control at 0 h incubation and 4 h postinfection showed no DNA fragmentation (FIG. 9, lanes 2 and 3).

(3). Western Blot

Figure 10:
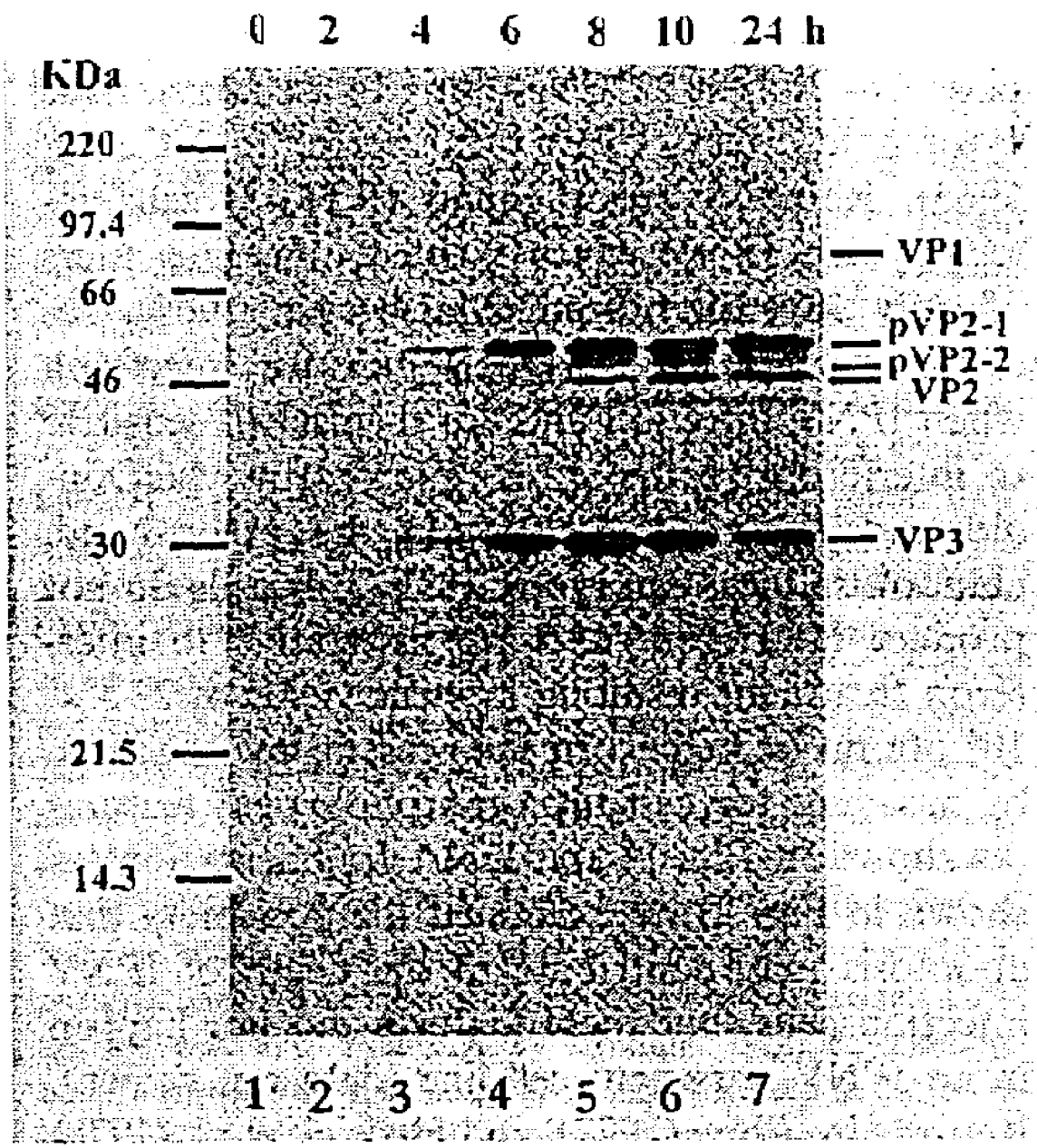
Figure 11:
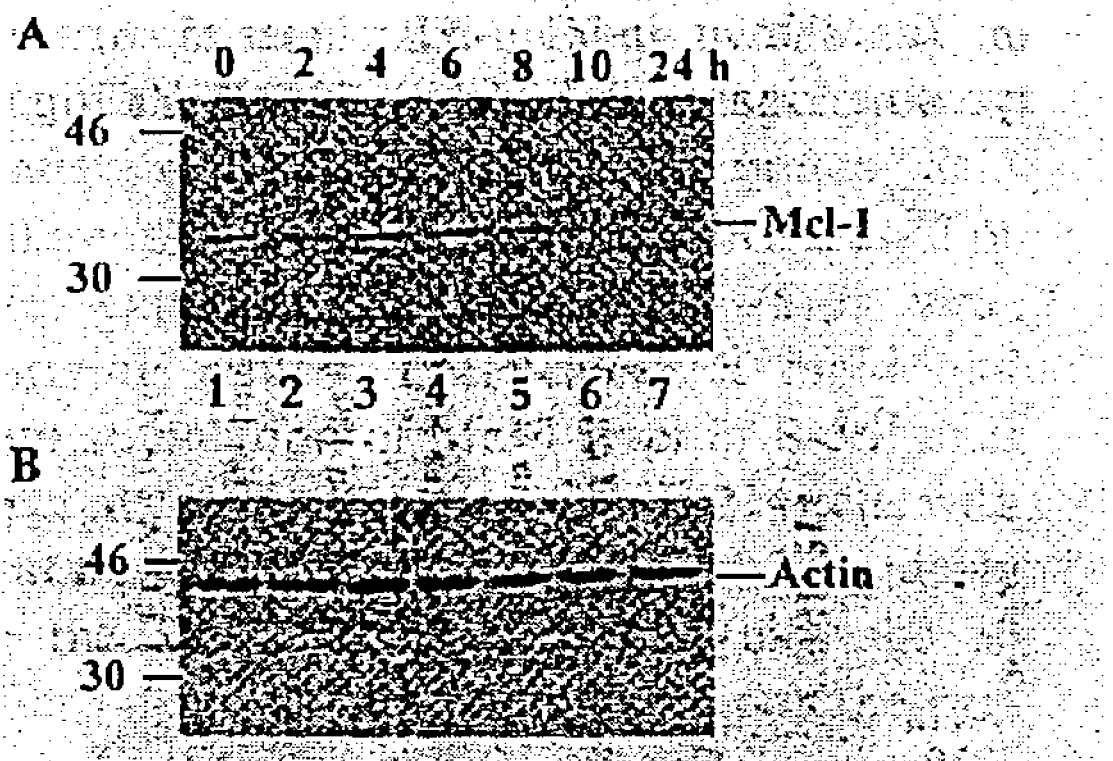

The characterization of the viral protein size and Mcl-1 expression was directly quantified by Western blots from CHSE-214 cells. FIG. 10 shows the major protein expression pattern during infection of CHSE-214 cells by a MOI of 1 of E1-S. The viral proteins had a large expression after 4 h post-infection. FIG. 11 shows the Mcl-1 protein expression pattern during infection of CHSE-214 cell with a MOI of 1of E1-S. The down-regulation of Mcl-1 expression occurred between 6 h and 8 h post-infection (as shown in FIG. 11A, lanes 4 and 5). The internal control actin is shown in FIG. 10B.

Figure 12:
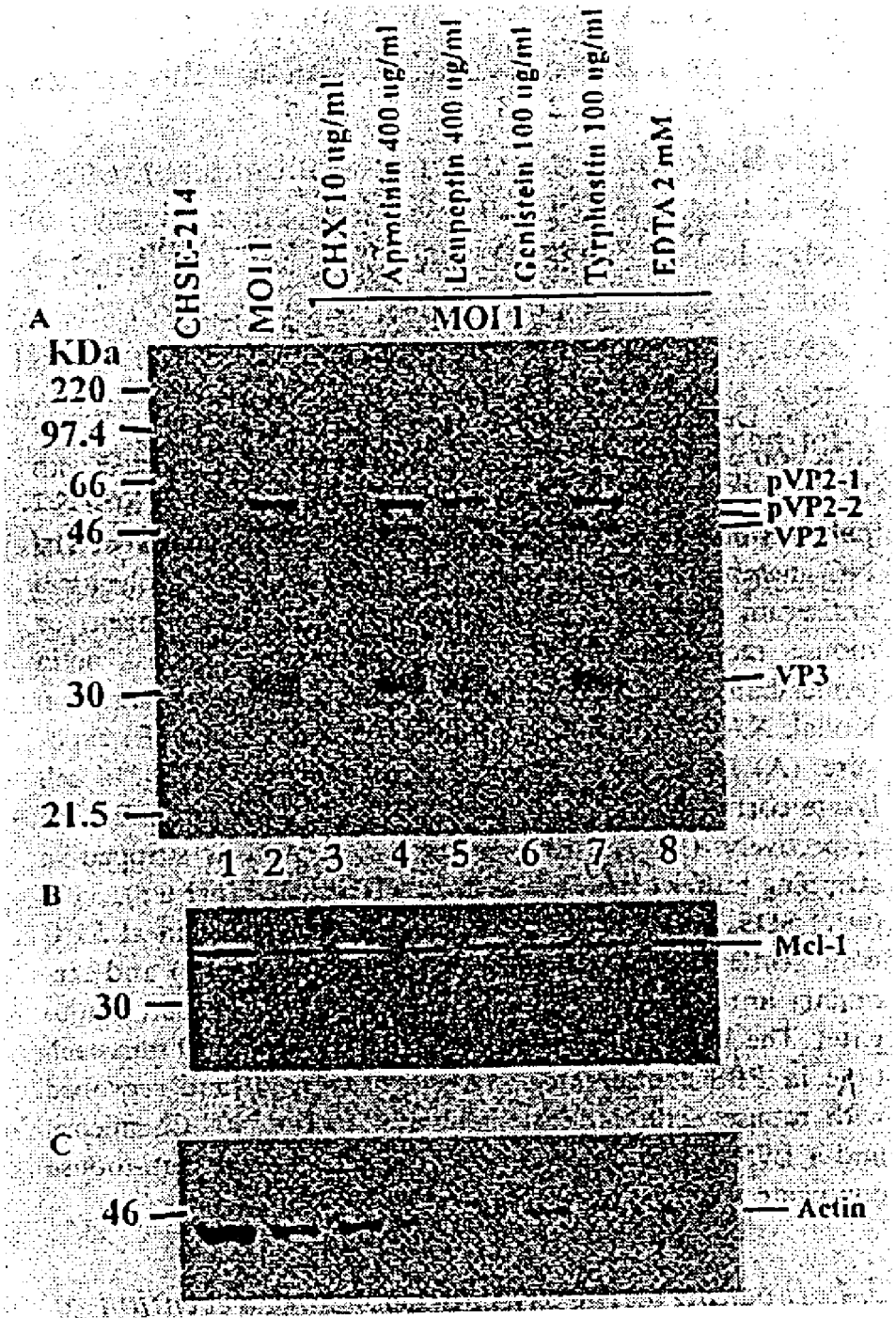
Figure 13:
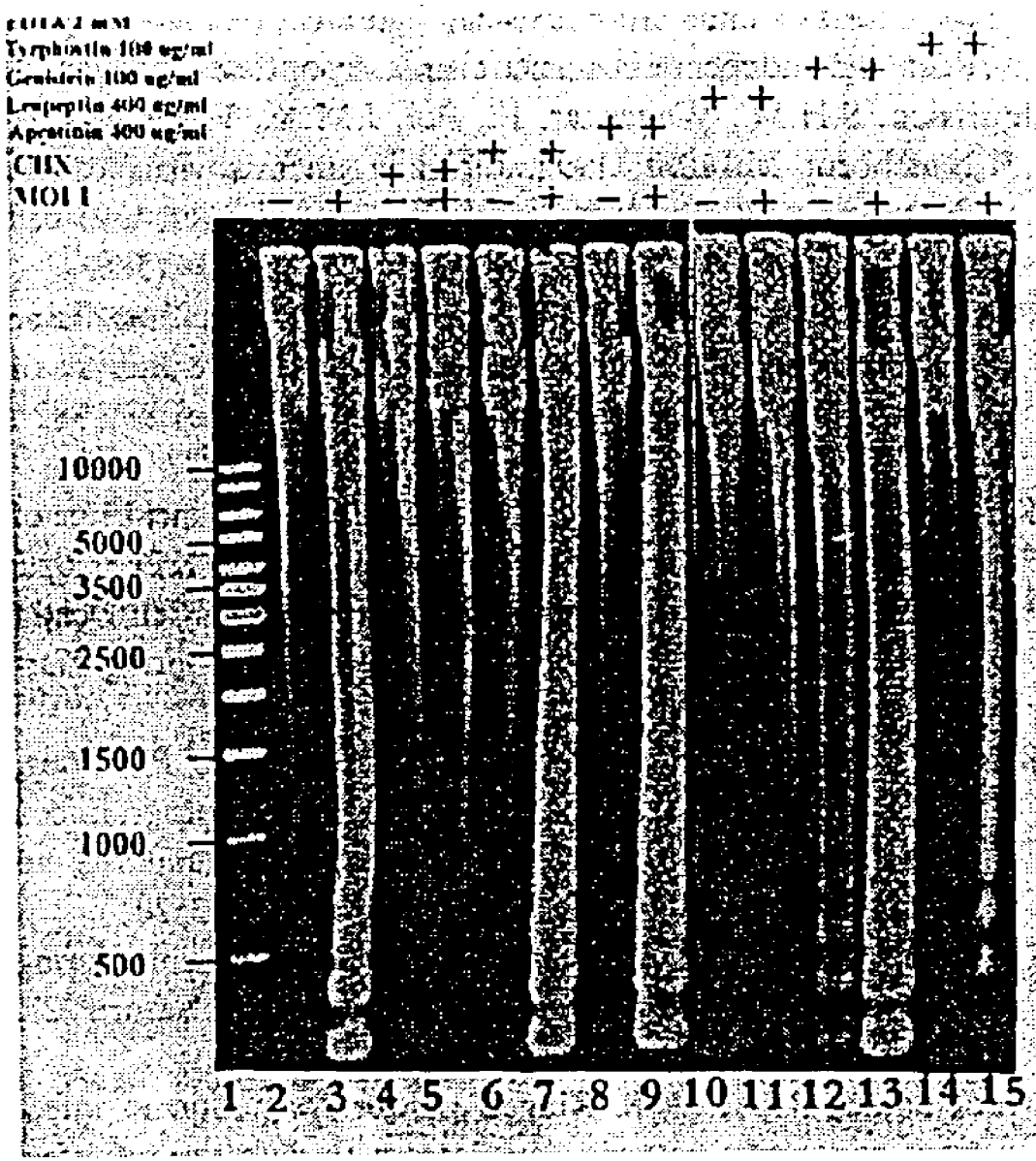

(4) Blocking of Virus Replication for Prevention of Down-Regulation of the Mcl-1 Protein by Certain Drugs To confirm whether viral replication is involved in down-regulation of Mcl-1, viral replication in host cell was blocked by treatment with certain drugs. When the protein synthesis inhibitors, 10 $\mu$g/ml cyclohexamide, tyrosine kinase inhibitor, 100 $\mu$g/ml of genistein or the cation chelator, 2 mM of EDTA, were added to CHSE-214 cells before IPNV infection, viral replication was prevented (as shown in FIG. 12A). At the same time, these same drugs partially prevented down-regulation of Mcl-1 protein expression (as shown in FIG. 12B). However, the serine proteinase inhibitor aprotinin 400 $\mu$g/ml and leupeptin 400 $\mu$g/ml (as shown in FIG. 12B, lanes 5–6) and the tyrosine kinase inhibitor tryphostin 100 $\mu$g/ml (as shown in FIG. 12B, lane 8) could not. The internal control actin protein is shown in FIG. 12C. The DNA internucleosomes were assayed under the same conditions described above. The blocking of viral replication groups consistently and strongly prevented the induction of internucleosomal cleavage by IPNV (as shown in FIG. 13), with the exception of the 2 mM EDTA treatment group which displayed minor internucleosomal cleavage (as shown in FIG. 13, lanes 14 and 15).

(5). Intact Cell System

Figure 14:
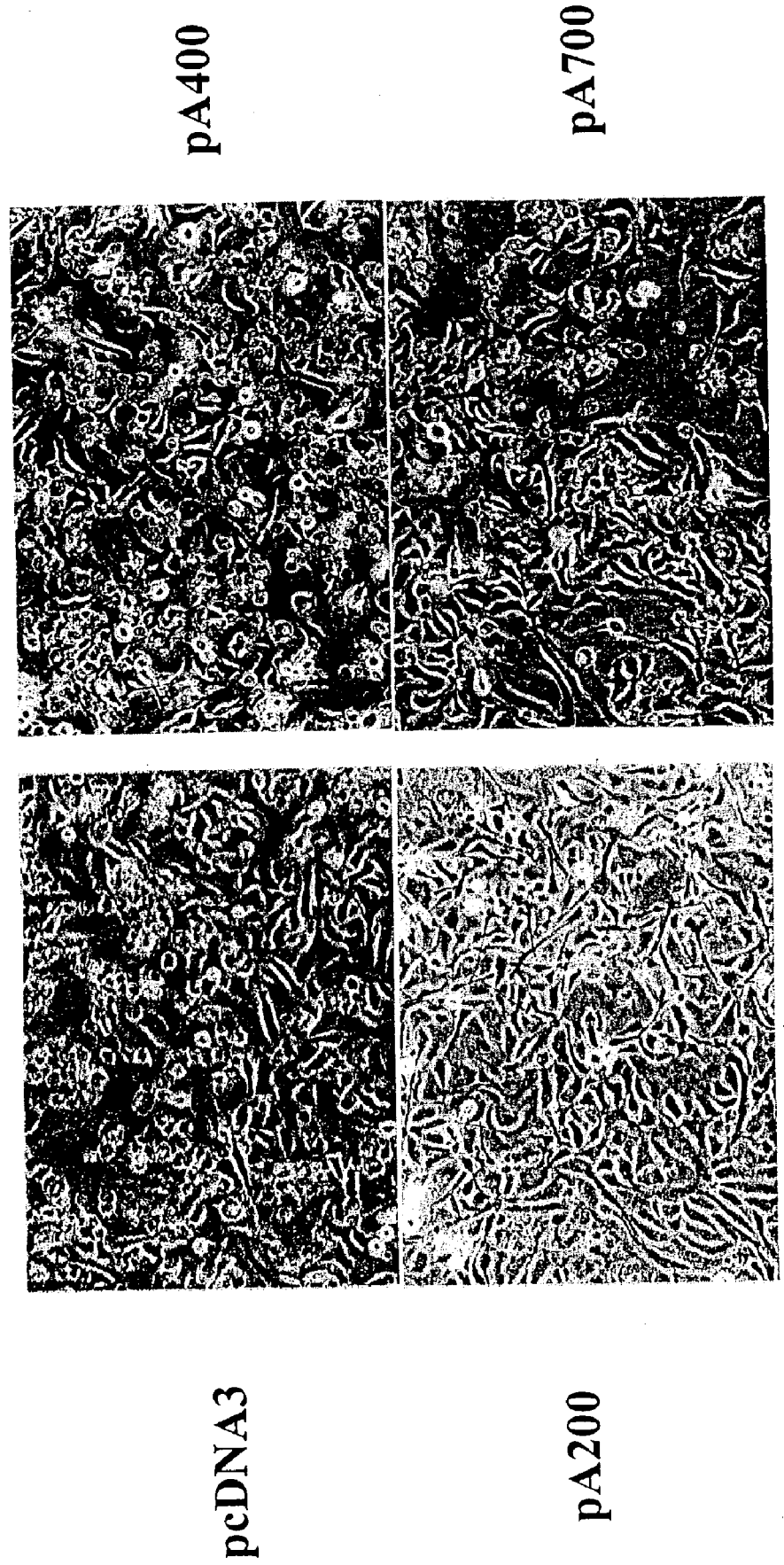
FIG. 14 shows that VP 3 antisense RNA could prevent cell death during IPNV infection in CHSE-214 cell lines at 24 hours post-infection (p.i.). pA200, pA400, and pA700 are plasmids containing various length (nucleotides) of VP3 antisense RNA (see infra for details). psDNA3 is a commercially available plasmid from Invitrogen, U.S.A., which is used as negative control.
Figure 15:
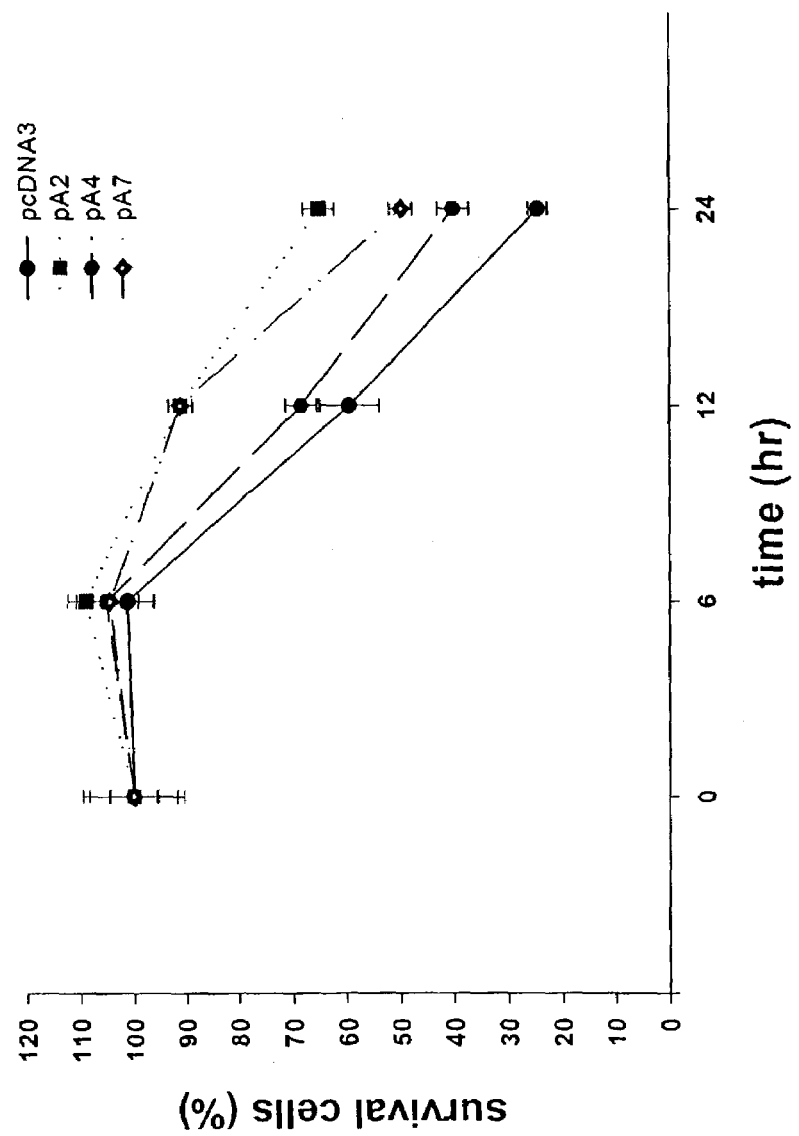
FIG. 15 shows that VP3 anti-sense RNA could knockdown VP3 death function and enhances the host cell survival during IPNV infection. The survival rate (%) of CHSE-214 cells with or without VP3 antisense RNA enhances cell survival during a 24 hours post infection with IPNV-E1S. pcDNA3 (24%); pA200 (67%); pA400 (42%); pA700 (48%).

In order to determine whether IPNV uses the VP3 protein in triggering host cell apoptosis, we designed different sized VP3 antisense RNA molecules (i.e., A200, A400, and A700) and inserted them into a blank plasmid pcDNA3 to form pA200 (nt. 501–711), pA400 (nt. 285–711) and pA700 (nt. 1–711) plasmids. These and blank insert pcDNA3 (Invitrogen, U.S.A.) and used selection with G418 to generate stable cell lines. The stable cells were then infected with IPNV (MOI 1). At the end of incubation time, the cell survival rate was assayed by use of the trypane blue method (results shown in FIG. 14 [phase-contrast images] and FIG. 15). In particular, at 24 hours post-incubation (p.i.), it was found that pA200 could increase survival up to 40%. VP3 antisense RNA molecules pA200, pA400 and pA700 were prepared using VP3 specific primers P1, P2, P3, and P4 for amplification. Specifically, VP3-specific primers P1 and P2 were used to amplify and generate A200, which contained base No. 501 to 711 of the VP3 antisense RNA, by PCR using taq polymerase; VP3-specific primers P1 and P3 were used to amplify and generate A400, which contained base No. 285 to 711 of the VP3 antisense RNA; VP3-specific primers P1 and P4 were used to amplify and generate A700, which contained base No. 1 to 711 of the VP3 antisense RNA. The A200, A400, and A700 VP3 antisense RNA molecules were constructed to pcDNA3.1/V5His-TOPO vector as pA200, pA400, and pA700, respectively.

(6). VP3 Gene Assay in Different Cell Lines

The fused gene, C1-EGFP-VP3, was inserted into a plasmid. pEGFP-C1 is a commercially available vector which contains a strong promoter (CMV promoter) and the EGFP gene. To produce the fused gene, VP3 gene was amplified using VP3-specific primers P1 and P2 by PCR and ligated to a pcDNA3.1 vector. The inserted VP3 in pcDNA3.1 vector was then cut with restriction enzymes HindIII and EcoRI, and re-constructed to a pEGFP-C1 vector from the HindIII and EcoRI sites. Individual gene function was tested in several different cell lines, including fish CHSE-214, mammalian cells NIH3T3 (Rat) and CHO (Hamster) cells and tumor cell as Hepa-3b and Hepa-G2 (Human). The EGFP-VP3 was transfected to cell lines with lipofectamine. Lipofectamine resembles a liposome which has the capability of forming a lipid bilayer to assist DNA transfection. VP3 induced NIH3T3 cell apoptosis (as shown in FIG. 16), as indicated by the percentage of positive apoptotic cells (as shown in FIG. 17) that were induced (about 20% at 36 hours p.i.). Apoptosis could be similarly induced by VP3 in other cell lines.

(7). VP3 Induced Zebrafish Embryonic Cell Death and Suppression by VP3 Antisense RNA Using zebrafish embryos as an in vivo assay system, one or two cell stage embryos were transfected with about 20 pg of VP3 using microinjection. (George Streisinger, "Zebrafish", University of Oregon Press, Edition 2.1, (1994)).

DNA fragmentation was analyzed in zebrafish embryonic cells injected with VP3. At end of the incubation time, the genomic DNA from the live and dead embryos was isolated and analyzed in 1.2% agarose gel (as shown in FIG. 18). It was found that VP3 induced embryo cell death by increasing DNA laddering (as shown in Lane 6 of FIG. 18), as compared to live embryos (as shown in Lanes 3 and 6 of FIG. 18) and with pEGFP-VP3 microinjection for 4 hours (as shown in Lane 5 of FIG. 18).

Overexpression of the PNV-VP3 induced embryonic cell death. Also shown is the micrographs of zebrafish embryos where apoptosis was triggered by microinjection with pEGFP-VP3 (as shown in FIGS. 19(C) & D), as contrasting to embryos microinjected with pEGFP-C1, the negative control (FIGS. 19(A) & (B)). Also, as shown in FIG. 19D, flattened dead cells and damaged somite appeared in the embryo microinjected with pEGFP-VP3 for 24 hours, probably due to overexpression of VP3. The damaged somite was more severe after 48 hours of microinjection with pEGFP-VP3 into zebrafish embryos, as seen in FIG. 20D.

Interestingly, when antisense RNA of VP3 was provided together with pEGFP-VP3, the % of alive embryos after microinjection with pEGFP-VP3 increased proportionally, as shown in FIG. 21, demonstrating that antisense VP3 RNA has the capability of overcoming cell death caused by overexpression of VP3. The same phenomenon was further supported by FIG. 21, where the % of defected embryos after 60 hours of microinjection with pEGFP-VP3 and pEGFP-VP3 plus antisense VP3 RNA was measured. In the group where pEGFP-VP3 plus antisense VP3 RNA was microinjected, the % of defected embryos was about 13%, contrasting to about 29% of defected embryos in the group where pEGFP-VP3 was microinjected. Further evidence showing that the leakage of defected zebrafish embryos was rescued by the addition of antisense VP3 RNA is provided in FIG. 23C.

(8). Bcl-2 Family Member, zfMcl-1a Block VP3 Death Function zfMcl-1a and zfBcl-xL were cloned by Chen et al (Chen M. C., Gong H. Y., Cheng C. Y., Wang J. P, Hong, J. R. and Wu J. L. (2000) Biochem. Biophys Res. Com. 279, 725–731). In order to test whether this protein could block VP3 function in zebrafish embryo, VP3 was microinjected along with zfMcl-1a or zfBcl-xL (1:1=20 pg:20 pg). The protocol for microinjection of VP3 and zfMcl-1a plasmid DNA was according to Chapter 5, George Streisinger, "Zebrafish", University of Orgon Press, Edition 2.1, (1994), which is herein incorporated by reference.

The results (FIGS. 24 and 25), which were determined after 36 hours of microinjection, demonstrate that zfMcl-1a enhanced embryonic survival by about 38% (FIG. 25, columns 3 and 4) and decreased embryonic defects about 20% (FIG. 24, columns 3 and 4).

(C) Discussion

IPNV is a highly contagious disease of susceptible hatchery-reared trout and Japanese eel in Taiwan. IPNV replicates in a variety of continuous cell lines from teleost fish at temperatures below 24° C. The virus replicates in the cytoplasm and a single cycle of replication takes 16–20 h at 22° C. resulting in a characteristic cytopathic effect (CPE). Rainbow trout gonad (RTG-2) cells infected with IPNV yielded infectious titers of only $10^6$-$\mathbf{10}^7$ pfu/M1, because the RTG-2 cells can produce interferon when IPNV infected and are themselves sensitive to interferon treatment, as reported by MacDonald and Kennedy (*Virology* (1979), 95:260–264). On the other hand, chinook salmon embryo (CHSE-214) cells do not produce interferon, and are insensitive to interferon treatment, resulting in virus yields of $2–5\times10^8$ pfu/ml or higher.

Figure 8:
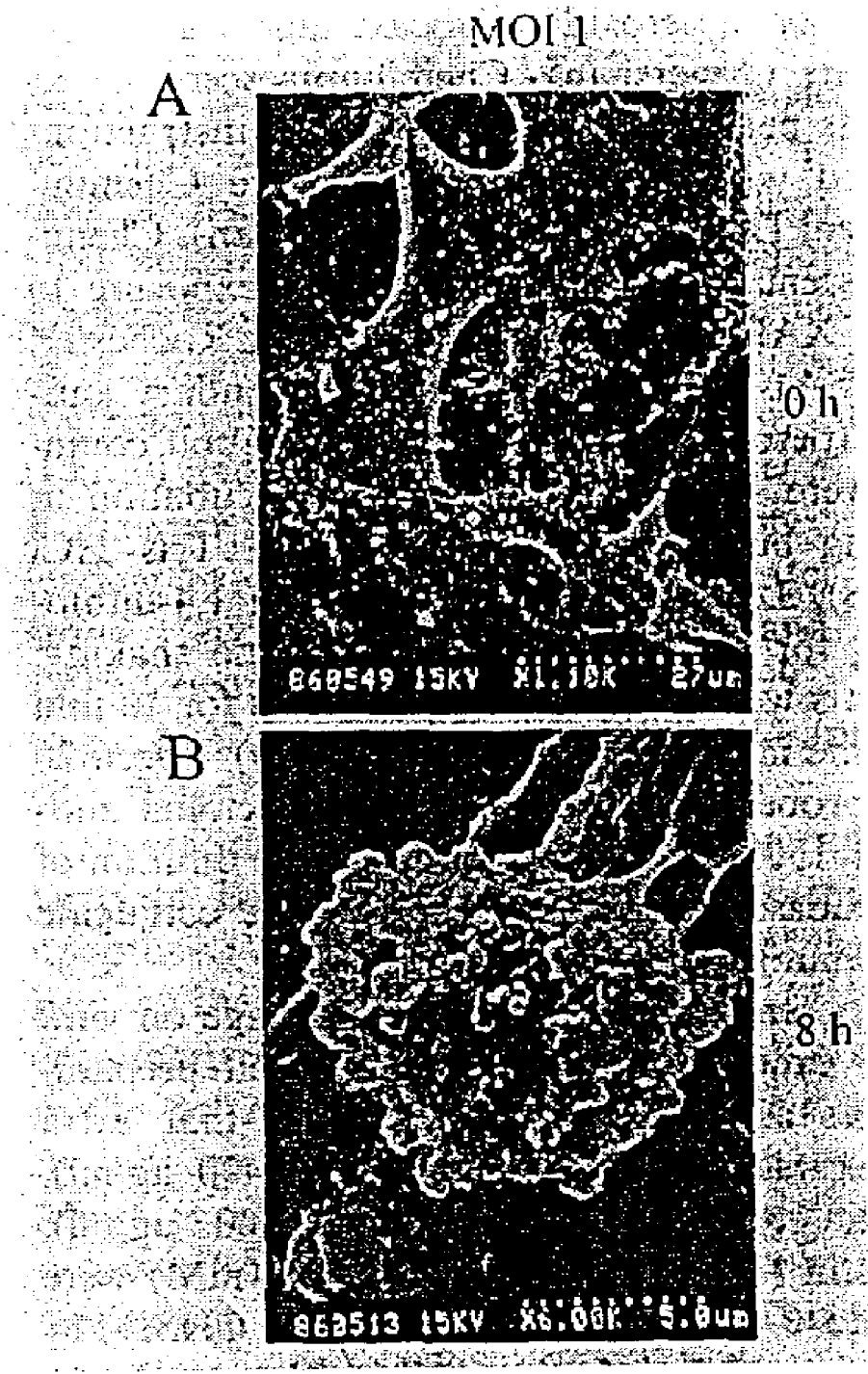

In the present invention, by assaying for cell ultra-morphological features (as shown in FIG. 8) and DNA fragmentation (as shown in FIG. 9), demonstrates that apoptosis contributed to the death of IPNV infected cells.

Also, viral replication (as shown in FIG. 10) correlates with down-regulation of Mcl-1 protein expression (as shown in FIG. 11A). This is the first study that confirms down-regulation of Mcl-1 (a member of the Bcl-2 family) protein expression by viral infection.

In view of the capacity of Mcl-1 to block or delay apoptosis and its sequence feature as a PEST (proline, glutamic acid, serine, threonine) protein that can be degraded rapidly, one possible role of this protein is as a rapid turnover effector that controls the rate of apoptosis. However, when treatment with some drugs before IPNV-infected CHSE-214 cells was performed, the protein synthesis inhibitor, cycloheximide, or the tyrosine kinase inhibitor, genistein, and the cation chelator, EDTA, all blocked viral protein expression (as shown in FIG. 12A). And at the same time, the same drugs helped to maintain Mcl-1 expression level (as shown in FIG. 12) and blocked the induction of DNA internucleosomal cleavage (as shown in FIG. 13) for rescue or delay of apoptotic cell death.

VP3, a 32-kDa protein derived from the IPNV segment A, induces apoptosis in fish CHSE-214 and mammalian cells, including the NIH3T3 (Mouse) and CHO (Hamster) cells and tumor cell as Hepa-3b and Hepa-G2 (Human). The results presented herein above demonstrate that VP3 can be suppressed by VP3 antisense RNA thereby enhancing the survival rate during IPNV infection. On the other hand, the VP3 expression alone can induce zebrafish embryonic cell death and DNA fragmentation. Death caused by VP3 can be prevented by anti-apoptosis protein zfMcl-1a, a Bcl-2 family member from zebrafish. It appears that VP3 is a functional death gene in late IPNV replication cycle that the effect of VP3 can be blocked by VP3 antisense RNA or functionally blocked by anti-apoptotic gene zfMcl-1a.

Having described the invention in detail and by reference to the preferred embodiments it will be apparent to those skilled in the art that modifications and variations are possible without departing from the scope of the invention as defined in the following appended claims.

We claim:

1. A method for or reducing preventing apoptosis in an fish cell induced by infectious pancreatic necrosis virus (IPNV) comprising:

treating said fish cell with an agent prior to IPNV infection, wherein said fish cell is challenged with IPNV infection, and said agent that is effective for preventing or reducing said apoptosis is one selected from the group consisting of cyclohexamide, genistein and EDTA.

2. The method according to claim 1, wherein said fish cell is one selected from the group consisting of rainbow trout cell (*Oncorhynchus mykiss*), brook trout cell (*Salvelinus fontinolis*), chinook salmon cell (*Oncorhynchus tshawytscha*), coho salmon cell (*Oncorhynchus kisutch*), sockeye salmon cell (*Oncorhynchus nerca*), Atlantic salmon cell (*Salmo salar*), carp cell, perch cell, pike cell, eels cell, char cell and Zebrafish cell.

3. The method according to claim 1, wherein said aquatic is treated with an effective amount of genistein.

4. The method according to claim 3, wherein said aquatic is chinook salmon.

* * * * *